US006824791B2

(12) United States Patent
Mathiowitz et al.

(10) Patent No.: US 6,824,791 B2
(45) Date of Patent: Nov. 30, 2004

(54) METHODS FOR MICRONIZATION OF HYDROPHOBIC DRUGS

(75) Inventors: Edith Mathiowitz, Brookline, MA (US); Christopher Thanos, Cumberland, RI (US); Zhi Liu, West Roxbury, MA (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 10/758,990

(22) Filed: Jan. 16, 2004

(65) Prior Publication Data

US 2004/0166168 A1 Aug. 26, 2004

Related U.S. Application Data

(63) Continuation of application No. 10/215,208, filed on Aug. 8, 2002, now Pat. No. 6,746,635.
(60) Provisional application No. 60/311,043, filed on Aug. 8, 2001.

(51) Int. Cl.[7] .............................. A61K 9/52; B32B 5/16
(52) U.S. Cl. ...................... 424/458; 264/4.3; 264/4.33; 264/4.6; 428/402.21; 428/402.24; 424/459; 424/462; 424/489
(58) Field of Search ................................ 264/4.3, 4.33, 264/4.6; 428/402.21, 402.24; 424/458, 459, 462, 489

(56) References Cited

U.S. PATENT DOCUMENTS

| | | |
|---|---|---|
| 4,211,578 A | 7/1980 | Scott, IV |
| 4,655,941 A | 4/1987 | Suzuki |
| 5,271,961 A | 12/1993 | Mathiowitz et al. |
| 5,298,355 A | 3/1994 | Tyagi et al. |
| 5,478,564 A | 12/1995 | Wantier et al. |
| 5,679,377 A | 10/1997 | Bernstein et al. |
| 5,718,921 A | 2/1998 | Mathiowitz et al. |
| 5,853,698 A | 12/1998 | Straub et al. |
| 5,876,756 A | 3/1999 | Takada et al. |
| 5,912,017 A | 6/1999 | Mathiowitz et al. |
| 5,922,355 A | 7/1999 | Parikh et al. |
| 5,955,096 A | 9/1999 | Santos et al. |
| 5,985,312 A | 11/1999 | Jacob et al. |
| 5,985,354 A | 11/1999 | Mathiowitz et al. |
| 6,022,564 A | 2/2000 | Takechi et al. |
| 6,042,792 A | 3/2000 | Shefer et al. |
| 6,113,795 A | 9/2000 | Subramaniam et al. |
| 6,117,455 A | 9/2000 | Takada et al. |
| 6,120,803 A | 9/2000 | Wong et al. |
| 6,123,965 A | 9/2000 | Jacob et al. |
| 6,143,211 A | 11/2000 | Mathiowitz et al. |
| 6,156,348 A | 12/2000 | Santos et al. |
| 6,193,951 B1 | 2/2001 | Ottoboni et al. |
| 6,197,346 B1 | 3/2001 | Mathiowitz et al. |
| 6,217,908 B1 | 4/2001 | Mathiowitz et al. |
| 6,235,224 B1 | 5/2001 | Mathiowitz et al. |
| 6,235,313 B1 | 5/2001 | Mathiowitz et al. |
| 6,248,720 B1 | 6/2001 | Mathiowitz et al. |
| 6,274,174 B1 | 8/2001 | Hom-ma et al. |
| 6,294,204 B1 | 9/2001 | Rossling et al. |
| 6,616,869 B2 | 9/2003 | Mathiowitz et al. |

FOREIGN PATENT DOCUMENTS

| | | |
|---|---|---|
| WO | WO 98/52544 A1 | 11/1998 |
| WO | WO 00/61113 A1 | 10/2000 |
| WO | WO 00/76483 | 12/2000 |
| WO | WO 01/26635 A2 | 4/2001 |
| WO | WO 01/51032 A2 | 7/2001 |

OTHER PUBLICATIONS

International Search Report dated Jan. 6, 2003 for PCT International Application No. PCT/US02/25134.

Primary Examiner—Samuel A. Acquah
(74) Attorney, Agent, or Firm—Wolf, Greenfield & Sacks, PC

(57) ABSTRACT

The invention involves methods and products related to the micronization of hydrophobic drugs. A method of micronizing hydrophobic drugs using a set of solutions including an aqueous solution is provided. The invention also relates to products of micronized hydrophobic drugs and related methods of use.

22 Claims, 12 Drawing Sheets

METHODS FOR MICRONIZATION OF HYDROPHOBIC DRUGS

RELATED APPLICATIONS

This application is a continuation of U.S. patent application Ser. No. 10/215,208, filed Aug. 8, 2002 now U.S. Pat. No. 6,746,635, "METHOD FOR MICRONIZATION OF HYDROPHOBIC DRUGS,", which is pending, which claims priority under U.S.C. §119(e) from U.S. Provisional Patent Application Ser. No. 60/311,043, filed Aug. 8, 2001, entitled "METHOD FOR MICRONIZATION OF HYDROPHOBIC DRUGS," The entire contents of all aforementioned applications are incorporated herein by reference.

GOVERNMENT SUPPORT

Aspects of the invention were made with Government support under Grant/Contract No. 2R01GM47636-05 awarded by the National Institute of Health. The Government may retain certain rights in this invention.

FIELD OF THE INVENTION

The invention relates to methods of micronizing hydrophobic drugs and related products and methods of using the micronized hydrophobic drugs.

BACKGROUND OF THE INVENTION

Many hydrophobic agents, both active and non-active have utility in a variety of in vivo settings. Although techniques exist for preparing and formulating hydrophobic agents, these techniques are limited. Some methods of formulation cause a loss of bioactivity. Other methods produce large drug particles or particles of inconsistent sizes that lead to problems in drug delivery.

One method for formulating hydrophobic agents involves the generation of microparticles. Microparticles, microcapsules and microspheres (hereinafter "microparticles") have important applications in the pharmaceutical, agricultural, textile and cosmetics industry as delivery vehicles. In these fields of application, a drug, protein, hormone, peptide, fertilizer, pesticide, herbicide, dye, fragrance or other agent is encapsulated in a polymer matrix and delivered to a site either instantaneously or in a controlled manner in response to some external impetus (i.e., pH, heat, water, radiation, pressure, concentration gradients, etc.). Microparticle size can be an important factor in determining the release rate of the encapsulated material.

Many microencapsulation techniques exist which can produce a variety of particle types and sizes under various conditions. Methods typically involve solidifying emulsified liquid polymer droplets by changing temperature, evaporating solvent, or adding chemical cross-linking agents. Physical and chemical properties of the encapsulant and the material to be encapsulated can sometimes dictate the suitable methods of encapsulation, making only certain methodologies useful in certain circumstances. Factors such as hydrophobicity, molecular weight, chemical stability, and thermal stability affect encapsulation. Significant losses are frequently associated with multiple processing steps. These parameters can be particularly important in respect of encapsulating bioactive agents because losses in the bioactivity of the material due to the processing steps or low yields can be extremely undesirable.

SUMMARY OF THE INVENTION

In some aspects, the invention involves a method of micronizing hydrophobic drugs. The micronized drugs prepared by these methods have a variety of properties that are advantageous in the field of drug delivery. For instance, the methods of the invention allow for the formation of particles that have an average particle size of less than 1 micron. The micronized drugs also exhibit enhanced crystallinity and may be used to prepare particles which result in improved relative bioavailability when administered to a subject. Several of these surprising properties are demonstrated in the examples section below.

According to one aspect of the invention, a method for micronizing a hydrophobic agent is provided. A hydrophobic agent is dissolved in an effective amount of a first solvent that is free of polymer. The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less.

According to another aspect of the invention, a method for micronizing a hydrophobic agent is provided. A hydrophobic agent is dissolved in an effective amount of a first solvent with a polymer. The hydrophobic agent and the first solvent form a mixture having a continuous phase. A second solvent and then an aqueous solution is introduced into the mixture. The introduction of the aqueous solution causes precipitation of the hydrophobic agent to produce a composition of micronized hydrophobic agent having an average particle size of 1 micron or less. In one embodiment, the final preparation contains less than 5% polymer. In yet another embodiment, the polymer is removed by the aqueous solution.

The hydrophobic agent may be dissolved in the first solvent in a variety of ways depending on the agent. Such methods include, but are not limited to, heating, sonicating, high shearing, or high stirring the hydrophobic agent in the first solvent.

The second solvent is optionally an alcohol selected from the group consisting of: methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, Di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-, pentanediol, and 3,5-pentanediol. A preferred alcohol is isopropanol. The second solvent may also be a mixture of alcohols selected from the aforementioned group.

Microparticles of the micronized hydrophobic agent may be prepared by a variety of methods including, for example, spray drying, interfacial polymerization, hot melt encapsulation, phase separation encapsulation, spontaneous emulsion, solvent evaporation microencapsulation, solvent removal microencapsulation, coacervation, and low temperature microsphere formation. One preferred method of preparing microparticles of the hydrophobic agent is by performing phase inversion nanoencapsulation (PIN).

According to another aspect of the invention, microparticles are provided. The microparticles may be produced by the processes described above. The microencapsulated product may be composed of particles having various sizes. In one embodiment, more than 90% of the particles have a size less than 1 micron.

According to still another aspect of the invention, a composition comprising a preparation of micronized hydrophobic agent having an average particle size of less than 1 micron is provided. The preparation is composed of less than 5% polymer carrier and is free of surfactant. In one embodiment, the preparation is free of polymer carrier.

The invention, also provides in some aspects a composition comprising a preparation of micronized hydrophobic agent having an average particle size of less than 1 micron, wherein the preparation is free of polymer carrier and wherein the crystallinity of the micronized hydrophobic agent is at least 50% of the crystallinity of the non-micronized hydrophobic agent. In one embodiment, the crystallinity is at least 75%. In another embodiment, the crystallinity is greater than 90%.

The invention also encompasses methods for delivering a hydrophobic agent to a subject, by administering an encapsulated product including the agent, to the subject. The solid preparation of the micronized hydrophobic agent having an average particle size of less than 1 micron, composed of less than 5% polymer and free of surfactant is administered orally. In one embodiment, the bioactivity of the hydrophobic agent is retained. In another embodiment, the micronized hydrophobic agent has at least a 5% increase in relative bioavailability compared to the non-micronized hydrophobic agent. In some embodiments, the preparation is free of polymer.

In other aspects, the invention provides methods for delivering an agent to a subject by administering microparticles of a micronized hydrophobic agent encapsulated by phase inversion nanoencapsulation. The average microparticle size is less than 1 micron and the preparation, is composed of less than 5% polymer and is free of surfactant. The microencapsulated micronized hydrophobic agent may be administered orally. In one embodiment, the bioactivity of the hydrophobic agent is retained. In another embodiment, the micronized hydrophobic agent has at least a 5% increase in relative bioavailability compared to the non-micronized hydrophobic agent. In some embodiments, the preparation is free of polymer.

The invention also provides a method for achieving 100% bioactivity. The method comprises orally administering to the subject a solid preparation of micronized hydrophobic agent having an average particle size of less than 1 micron wherein 100% of the orally administered agent is bioactive. In an embodiment, the preparation is composed of less than 5% polymer and is free of surfactant. In some embodiments, the preparation is free of polymer.

The foregoing aspects of the invention as well as various objects, features, and advantages are discussed in greater detail below.

DETAILED DESCRIPTION

Figure 1A:
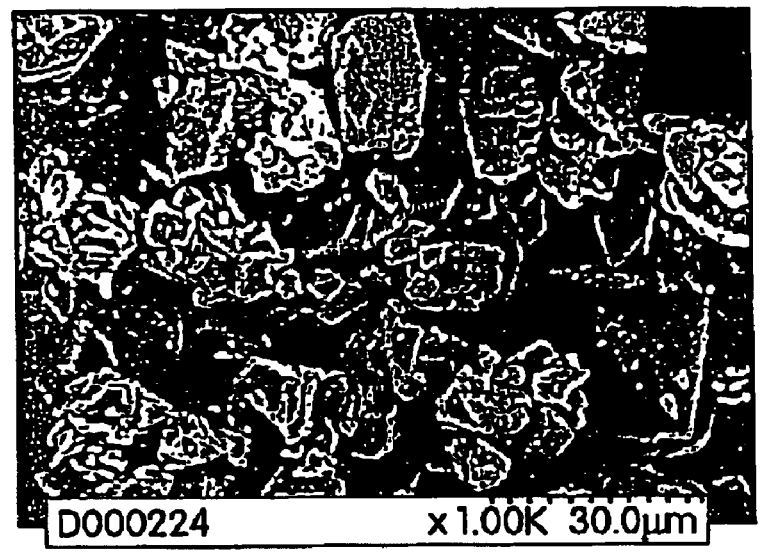
FIG. 1. SEM micrographs of dicumarol formulations. (A) Stock Dicumarol, (B) Spray-Dried Dicumarol, (C) Micronized Dicumarol, and (D) Dicumarol in pFA:SA.

The invention is based, in some aspects, on a new method for micronizing hydrophobic agents. It was discovered according to the invention that the method for micronizing hydrophobic agents results in a product having enhanced properties which lead to better plasma concentration in vivo administration. For instance, the micronized agent has reduced particle size, increased crystallinity and enhanced bioactivity and relative bioavailability when administered to a subject. The dramatic increases in bioactivity and relative bioavailability were unexpected.

The micronized agent prepared according to the methods of the invention may be used directly, e.g., administered to a subject, or it may be further manipulated into pharmaceutical compositions, such as microparticles. As shown in the Examples section, when the micronized agent was used to produce microparticles and those microparticles were delivered to animals the relative bioavailability increased dramatically compared to non-micronized formulations. In Example 4 it was demonstrated that these microparticles were capable of achieving close to and in some instances more than 100% relative bioavailability when orally administered (Table 4). Relative bioavailability as used herein refers to the amount of a drug available for detection in the systemic circulation as compared to an administered IV dose. The relative bioavailability of a drug administered by a route other than IV, is generally a function of the ability of the drug to permeate and penetrate into the systemic circulation. Relative bioavailability is affected by a variety of factors, most importantly permeability and solubility of the drug. Although absolute (100%) bioavailability might be achieved with IV administration, difficulties and limitations may be encountered in IV administration (such as drug precipitation/crystallinization in the blood) which render bioavailabity relative rather than absolute. If a drug administered by IV undergoes precipitation or crystallization, then the same drug administered by a different route may in some cases have a relative bioavailability greater than 100%.

The method in some aspects involves the formation of a continuous phase mixture or preparation of the hydrophobic agent to be micronized and a first solvent. This mixture or preparation is free of polymer. As used herein, a mixture or a preparation free of polymer refers to a mixture or preparation that has no detectable amount of polymer.

In some aspects of the invention, the mixture or preparation is substantially free of polymer. As used herein, substantially free of polymer is more than 97% free of polymer. In some embodiments the mixture or preparation is more than 98%, or more than 99%, or 100% free of polymer. In some embodiments, the mixture or preparation is absolutely free of polymer. As used herein absolutely free of polymer refers to a mixture or preparation that is 100% free of polymer.

The method may be accomplished by dissolving or dispersing the hydrophobic agent Is in an effective amount of the solvent. A second solvent that is immiscible with the original solvent and an aqueous solution are introduced into the mixture. The introduction of the aqueous solution causes the precipitation of the hydrophobic agent to produce a micronized drug.

The micronized hydrophobic agent may be used without further manipulation. For instance, it may be administered directly to a subject. The micronization procedure transforms the hydrophobic agent from a compound which when delivered directly to a subject has low relative bioavailability into one which, because of the micronized properties, has a much higher relative bioavailability when administered. Although it is not necessary, it is also possible to further process the micronized agent to produce microparticles or to incorporate the agent into other drug delivery devices. Microparticles of the micronized hydrophobic agent can be prepared by several common microencapsulation techniques. Suitable methods of encapsulation may be selected to produce the desired physical and chemical properties of the encapsulant and the material to be encapsulated. These optional methods are described in more detail below.

The methods are particularly useful for micronizing hydrophobic agents. The hydrophobic agent may be any type of hydrophobic compound including active agents and non-active agents. The hydrophobic agent is an agent that does not adsorb or absorb water. Hydrophobic active and non-active agents include, but are not limited to, adhesives, gases, pesticides, herbicides, fragrances, antifoulants, dies, salts, oils, inks, cosmetics, catalysts, detergents, curing agents, flavors, foods, fuels, metals, paints, photographic agents, biocides, pigments, plasticizers, propellants and the like. The active agent also may be a bioactive agent. The bioactive agent may be, for example, adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastrointestinal motility effector; glucocorticoid; hair growth stimulant; hemostatic; histamine $H_2$ receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine Al antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor; Anti-cancer, e.g. paclitaxel.

Bioactive agents also include immunological agents such as allergens (e.g., cat dander, birch pollen, house dust, mite, grass pollen, etc.) and antigens from pathogens such as viruses, bacteria, fungi and parasites. These antigens may be in the form of whole inactivated organisms, peptides, proteins, glycoproteins, carbohydrates or combinations thereof. Specific examples of pharmacological or immunological agents that fall within the above-mentioned categories and that have been approved for human use may be found in the published literature.

The hydrophobic agent is added to and dissolved in a first solvent. The first solvent is any suitable solvent that is capable of dissolving the hydrophobic agent. Typically the solvent will be a common organic solvent such as a halogenated aliphatic hydrocarbon such as methylene chloride, chloroform and the like; an alcohol; an aromatic hydrocarbon such as toluene; a halogenated aromatic hydrocarbon; an ether such as methyl t-butyl; a cyclic ether such as tetrahydrofuran; ethyl acetate; diethylcarbonate; acetone; or cyclohexane. The solvents may be used alone or in combination as the first solvent. It is desirable that the solvent be inert with respect to the agent being micronized. Those of skill in the art will be able to select an appropriate first solvent for the particular hydrophobic agent being micronized based on the guidance provided herein.

In some embodiments the hydrophobic agent is dissolved in an effective amount of the first solvent with a polymer. When a polymer is present in the first solvent, the agent is added to the solvent optionally after the polymer is dissolved in the solvent. If a polymer is used, the solvent chosen should be capable of dissolving the polymer, and it is desirable that the solvent be inert with respect to the polymer. It is preferred that the final product has a low concentration of polymer or no polymer at all. This could be achieved by choosing a polymer that is slightly soluble in water, or else a polymer that degrades in water. This way some of the polymer will disappear from the final formulation.

A "polymer" may be any suitable (micronizing) material consisting of repeating units including, but not limited to, nonbioerodible and bioerodible polymers. As used herein the term "polymer" includes polymer carriers and surfactants. A "polymer carrier" is a polymer that does not function as a surfactant. A surfactant is a surface-active agent that modifies the nature of surfaces, i.e., which may involve reducing the surface tension of water. Surfactants include but are not limited to wetting agents, detergents, emulsifiers, dispersing agents, penetrants, and antifoams. Some surfactants are polymers and others are non-polymeric. Thus only a subset of surfactants are polymeric surfactants.

Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate), poly vinyl chloride polystyrene and polyvinylpryrrolidone.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters; polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. Some preferred polymers are polyesters, polyanhydrides, polystyrenes and blends thereof.

Bioadhesive polymers are also useful. A bioadhesive polymer is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). These are particularly useful when the particles formed by the methods of the invention are delivered orally or to other mucosal tissue.

Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups. Numerous bioadhesive polymers are discussed in WO 93/21906. Representative bioadhesive polymers of particular interest include bioerodible hydrogels described by H. S. Sawhney, C. P. Pathak and J. A. Hubell in Macromolecules. 1993, 26:581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly butylmethacrylate), poly(isobutylmethacrylate), poly(hexlmethacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate). A preferred polymer is poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers may be combined with metal oxide particles to improve bioadhesion even more than with the organic additives alone. Organic dyes because of their electronic charge and hydrophobicity/hydrophilicity can either increase or decrease the bioadhesive properties of polymers when incorporated into the polymers. The incorporation of oligomer compounds into a wide range of different polymers that are not normally bioadhesive dramatically increases their adherence to tissue surfaces such as mucosal membranes.

As used herein, the term "anhydride oligomer" refers to a diacid or polydiacids linked by anhydride bonds, and having carboxy end groups linked to a monoacid such as acetic acid by anhydride bonds. The anhydride oligomers have a molecular weight less than about 5000, typically between about 100 and 5000 daltons, or are defined as including between one to about 20 diacid units linked by anhydride bonds. In one embodiment, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer is hydrolytically labile. As analyzed by gel permeation chromatography, the molecular weight may be, for example, on the order of 200–400 for fumaric acid oligomer (FAPP) and 2000–4000 for sebacic acid oligomer (SAPP). The anhydride bonds can be detected by Fourier transform infrared spectroscopy by the characteristic double peak at 1750 $cm^{-1}$ and 1820 $cm^{-1}$, with a corresponding disappearance of the carboxylic acid peak normally at 1700 $cm^{-1}$.

In one embodiment, the oligomers may be made from diacids described for example in U.S. Pat. No. 4,757,128 to Domb et al., U.S. Pat. No. 4,997,904 to Domb, and U.S. Pat. No. 5,175,235 to Domb et al., the disclosures of which are incorporated herein by reference. For example, monomers such as sebacic acid, bis(p-carboxy-phenoxy)propane, isophathalic acid, fumaric acid, maleic acid, adipic acid or dodecanedioic acid may be used.

Organic dyes, because of their electronic charge and hydrophilicity/hydrophobicity, may alter the bioadhesive properties of a variety of polymers when incorporated into the polymer matrix or bound to the surface of the polymer. A partial listing of dyes that affect bioadhesive properties include, but are not limited to: acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2, 3, 13 and 86, rose bengal, safranin o, Sudan III and IV, Sudan black B and toluidine blue.

The working molecular weight range for the polymer is on the order of 1 kDa-150,000 kDa, although the optimal range is 2 kDa-50 kDa. The working range of polymer concentration is 0.01–50% (weight/volume), depending primarily upon the molecular weight of the polymer and the resulting viscosity of the polymer solution. In general, the low molecular weight polymers permit usage of a higher concentration of polymer. A preferred concentration range according to the invention may be on the order of 0.0%–10% (weight/volume), while the optimal polymer concentration in the micronized product typically will be below 5% and preferably be close to or equal to 0%. It has been found that polymer concentrations on the order of 0–5% are particularly useful according to the methods of the invention.

The hydrophobic agent and the first solvent (with or without a polymer) form a continuous mixture. The hydrophobic agent is dissolved in the first solvent by any of a variety of methods, depending on the type of agent. Preferred methods include heating, sonicating, high shearing, or stirring the hydrophobic agent in the first solvent.

A second solution is then introduced into the mixture. The "second solvent" as used herein is a solvent that is immiscible with the original solvent. The second solvent includes, for example, any suitable alcohol or a combination of alcohols. Typically the solvent will be a common alcohol. Preferred alcohols are methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, Di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, and 3,5-pentanediol. The most preferred alcohol is isopropanol. One or more of the alcohols can be used in combination.

An aqueous solution is then introduced into the above mixture. The addition of the aqueous solution causes precipitation of the hydrophobic agent and produces a composition of micronized agent. An "aqueous solution" as used herein is a solution in which water is the only or main component. The first and second solvents are selected such that when these two immiscible solvents are added to the aqueous solution, the three solutions become miscible.

The micronized hydrophobic agent may be used without further manipulation. For instance, it may be administered directly to a subject. Alternatively, the micronized hydrophobic agent may be further processed prior to use, e.g. it may be processed to produce microparticles. Microparticles of the micronized hydrophobic agent may be prepared using any one of several common microencapsulation techniques. Different microencapsulation techniques produce a variety of microparticles having different properties under various conditions. Suitable methods of encapsulation may be selected to produce the desired physical and chemical properties of the encapsulant and the material to be encapsulated. As used herein the terms "microparticle" and "microencapsulation" are used broadly to refer to particles, spheres or capsules that have sizes on the order of microns as well as nanometers. Thus, the terms "microparticle" "microsphere", "nanoparticle", "nanosphere", "nanocapsule" and "microcapsule" are used interchangeably.

Common microencapsulation techniques include but are not limited to spray drying, interfacial polymerization, hot melt encapsulation, phase separation encapsulation (solvent removal and solvent evaporation), spontaneous emulsion, solvent evaporation microencapsulation, solvent removal microencapsulation, coacervation, and low temperature microsphere formation and phase inversion nanoencapsulation (PIN). Each of these methods is well known in the art. A brief summary of the methods is presented below.

In spray drying, the core material to be encapsulated is dispersed or dissolved in a solution. Typically, the solution is aqueous and preferably the solution includes a polymer. The solution or dispersion is pumped through a micronizing nozzle driven by a flow of compressed gas, and the resulting aerosol is suspended in a heated cyclone of air, allowing the solvent to evaporate from the microdroplets. The solidified microparticles pass into a second chamber and are trapped in a collection flask.

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

In hot melt microencapsulation the core material (to be encapsulated) is added to molten polymer. This mixture is suspended as molten droplets in a nonsolvent for the polymer (often oil-based) which has been heated to approximately 10° C. above the melting point of the polymer. The emulsion is maintained through vigorous stirring while the nonsolvent bath is quickly cooled below the glass transition of the polymer, causing the molten droplets to solidify and entrap the core material.

In solvent evaporation microencapsulation, the polymer is typically dissolved in a water immiscible organic solvent and the material to be encapsulated is added to the polymer solution as a suspension or solution in organic solvent. An emulsion is formed by adding this suspension or solution to a beaker of vigorously stirring water (often containing a surface active agent to stabilize the emulsion). The organic solvent is evaporated while continuing to stir. Evaporation results in precipitation of the polymer, forming solid microcapsules containing core material.

The solvent evaporation process is designed to entrap a liquid core material in PLA, PLA/PGA copolymer, or PLA/PCL copolymer microcapsules. The PLA or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the PLA or copolymer to phase separate and migrate towards the surface of the core material droplets. This phase separated solution is then transferred into an agitated volume of nonsolvent, causing any remaining dissolved PLA or copolymer to precipitate and extracting any residual solvent from the formed membrane. The result is a microcapsule composed of PLA or copolymer shell with a core of liquid material.

In solvent removal microencapsulation, the polymer is typically dissolved in an oil miscible organic solvent and the material to be encapsulated is added to the polymer solution as a suspension or solution in organic solvent. An emulsion is formed by adding this suspension or solution to a beaker of vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

In phase separation microencapsulation, the material to be encapsulated is dispersed in a polymer solution by stirring. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

Spontaneous emulsification involves solidifying emulsified liquid polymer droplets by changing temperature, evaporating solvent, or adding chemical cross-linking agents. Physical and chemical properties of the encapsulant and the material to be encapsulated dictates the suitable methods of encapsulation. Factors such as hydrophobicity, molecular weight, chemical stability, and thermal stability affect encapsulation.

In solvent evaporation microencapsulation, the polymer is typically dissolved in a water immiscible organic solvent and the material to be encapsulated is added to the polymer solution as a suspension or solution in organic solvent. An emulsion is formed by adding this suspension or solution to a beaker of vigorously stirring water (often containing a surface active agent to stabilize the emulsion). The organic solvent is evaporated while continuing to stir. Evaporation results in precipitation of the polymer, forming solid microcapsules containing core material, containing the micronized hydrophobic agent.

Some solvent evaporation processes are specifically designed to entrap a liquid core material in PLA, PLA/PGA copolymer, or PLA/PCL copolymer microcapsules. The PLA or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the PLA or copolymer to phase separate and migrate towards the surface of the core material droplets. This phase separated solution is then transferred into an agitated volume of nonsolvent, causing any remaining dissolved PLA or copolymer to precipitate and extracting any residual solvent from the formed membrane. The result is a microcapsule composed of PLA or copolymer shell with a core of liquid material containing micronized hydrophobic agent.

In solvent removal microencapsulation, the polymer is typically dissolved in an oil miscible organic solvent and the material to be encapsulated is added to the polymer solution as a suspension or solution in organic solvent. An emulsion is formed by adding this suspension or solution to a beaker of oil with vigorous stirring, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

Encapsulation procedures for various substances using coacervation techniques have been described in the prior art, for example, in GB-B-929 406; GB-B-929 40 1; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142–143).

Through the process of coacervation compositions comprised of two or more phases and known as coacervates may be produced. The ingredients that comprise the two phase coacervate system are present in both phases; however, the colloid rich phase has a greater concentration of the components than the colloid poor phase.

Components that may be used to formulate the coacervate system comprise anionic, cationic, amphoteric, and non-ionic surfactants. Anionic surfactants include di-(2 ethylhexyl) sodium sulfosuccinate; non-ionic surfactants include the fatty acids and the esters thereof; surfactants in the amphoteric group include (1) substances classified as simple, conjugated and derived proteins such as the albumins, gelatins, and glycoproteins, and (2) substances contained within the phospholipid classification, for example lecithin. The amine salts and the quaternary ammonium salts within the cationic group also comprise useful surfactants. Other surfactant compounds useful to form coacervates include compositions within the groups known as the polysaccharides and their derivatives, the mucopolysaccharides and the polysorbates and their derivatives. Synthetic polymers that may be used as surfactants include compositions such as polyethylene glycol and polypropylene glycol. Further examples of suitable compounds that may be utilized to prepare coacervate systems include glycoproteins, glycolipids, galactose, gelatins, modified fluid gelatins and galacturonic acid.

In addition, substances that are not intrinsically surface active may be used to prepare coacervates provided that they can be made so by chemical or other means. Fatty acids are not considered to be surface active compounds. However, when fatty acids are reacted with an alkaline chemical entity the resulting products will have surface-active properties.

Low temperature microsphere formation has been described, see, e.g., U.S. Pat. No. 5,019,400. The method is a process for preparing microspheres which involves the use of very cold temperatures to freeze polymer-biologically active agent mixtures into polymeric microspheres. The polymer is generally dissolved in a solvent together with an active agent that can be either dissolved in the solvent or dispersed in the solvent in the form of microparticles. The polymer/active agent mixture is atomized into a vessel containing a liquid non-solvent, alone or frozen and overlayed with a liquefied gas, at a temperature below the freezing point of the polymer/active agent solution. The cold liquefied gas or liquid immediately freezes the polymer droplets. As the droplets and non-solvent for the polymer is warmed, the solvent in the droplets thaws and is extracted into the non-solvent, resulting in hardened microspheres.

Phase separation microencapsulation proceeds more rapidly than the procedures described in the preceding paragraphs. A polymer is dissolved in the solvent. An agent to be encapsulated then is dissolved or dispersed in that solvent. The mixture then is combined with an excess of nonsolvent and is emulsified and stabilized, whereby the polymer solvent no longer is the continuous phase. Aggressive emulsification conditions are applied in order to produce microdroplets of the polymer solvent. After emulsification, the stable emulsion is introduced into a large volume of non-solvent to extract the polymer solvent and form microparticles. The size of the microparticles is determined by the size of the microdroplets of polymer solvent.

One method for microencapsulating the micronized hydrophobic agent is by phase inversion nanoencapsulation (PIN). In PIN, a polymer is dissolved in an effective amount of a solvent. The agent to be encapsulated is also dissolved or dispersed in the effective amount of the solvent. The polymer, the agent and the solvent together form a mixture having a continuous phase, wherein the solvent is the continuous phase. The mixture is introduced into an effective amount of a nonsolvent to cause the spontaneous formation of the microencapsulated product, wherein the solvent and the nonsolvent are miscible. PIN has been described by Mathiowitz et al. in U.S. Pat. No. 6,131,211 and U.S. Pat. No. 6,235,224 that are incorporated herein by reference.

Thus, the invention also provides compositions of the micronized hydrophobic agent or microparticles produced using the micronized hydrophobic agent by the processes described above as well as other processes known in the art. The microencapsulated product or micronized hydrophobic agent consist of particles having various sizes. In some embodiments the particles have an average particle size of less than one micron. In other embodiments more than 90% of the particles have a size less than 1 micron.

The compositions of the invention have some properties which are advantageous over prior art products. For instance, the preparation of micronized hydrophobic agent has enhanced crystallinity over that of similar prior art preparations. The micronized hydrophobic agent of the invention may have at least 50% of the crystallinity of a non-micronized hydrophobic agent. In some embodiments it has at least 75%, 80%, 85%, 90%, or 95% of the crystallinity of a non-micronized hydrophobic agent. As used herein the term crystallinity refers to a property of a preparation having a body that is formed by the solidification of a chemical element, a compound, or a mixture and has a regularly repeating internal arrangement of its atoms and often external plane faces. The crystallinity of a preparation may be determined by methods known in the art. Some of the methods of measuring crystallinity are described in Introduction to Polymers, 2nd Edition; Young RJ, Lovell PA. 1991, Chapman and Hall Publishing, London, UK. One of the methods to measure crystallinity is thermal analysis. An example of this type of analysis is presented in Example 1 below. The magnitude of thermal change is proportional to the amount of crystalline component. A compound having enhanced crystallinity has improved release properties when administered in vivo.

As demonstrated in the Examples below, the compositions of the invention also allow for enhanced bioactivity and relative bioavailability of the hydrophobic agent. Many drug processing techniques result in a loss of bioactivity of the drug. The micronization process described herein is sufficient to allow the drug to retain its bioactivity. As a result, when the drug is delivered to a subject the drug is active. As used herein bioactivity refers to the normal function of a known drug. It refers to the presence or absence of a function and can be used to describe relative changes in levels of function rather than an absolute value.

The micronized hydrophobic agent also exhibits at least a 5% increase in relative bioavailability compared to the non-micronized hydrophobic agent. The dramatic difference in relative bioavailability of in vivo administered micronized agent versus non-micronized agent is demonstrated in the Examples. When administered through different routes, such as orally, the micronized hydrophobic agent exhibited dramatically increased relative bioavailability.

The compositions may include a physiologically or pharmaceutically acceptable carrier, excipient, or stabilizer mixed with the micronized hydrophobic agent. The term "pharmaceutically acceptable" means a non-toxic material that does not interfere with the effectiveness of the biological activity of the active ingredients. The term "pharmaceutically-acceptable carrier" means one or more compatible solid or liquid filler, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The micronized hydrophobic agent may be administered per se or in the form of a pharmaceutically acceptable salt. When used in medicine the salts may be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1–2% w/v); citric acid and a salt (1–3% w/v); boric acid and a salt (0.5–2.5% w/v); and phosphoric acid and a salt (0.8–2% w/v). Suitable preservatives include benzalkonium chloride (0.003–0.03% w/v); chlorobutanol (0.3–0.9% w/v); parabens (0.01–0.25% w/v) and thimerosal (0.004–0.02% w/v).

Pharmaceutical formulations for parenteral administration include aqueous solutions of the micronized hydrophobic agent in water-soluble form. Additionally, suspensions of the micronized hydrophobic agent may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The micronized hydrophobic agent may be administered by any ordinary route for administering medications. Depending upon the type of disorder to be treated, the micronized hydrophobic agent of the invention may be inhaled, ingested or administered by systemic routes. Systemic routes include oral and parenteral. For use in therapy, an effective amount of the micronized hydrophobic agent can be administered to a subject by any mode that delivers the nucleic acid to the organ or tissue being treated or monitored. Preferred routes of administration include but are not limited to, oral, parenteral, intramuscular, intranasal, intratracheal, intrathecal, intravenous, inhalation, transdermal, intratracheobronchial (including intrapulmonary), ocular, vaginal, and rectal.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres, as described above, formulated for oral administration may also be used. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Inhaled medications are preferred in some embodiments because of the direct delivery to the lung. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components which will not significantly impair the biological properties of the agent (see, for example, Sciarra and Cutie, "Aerosols," in Remington's Pharmaceutical Sciences, 18th edition, 1990, pp. 1694–1712; incorporated by reference).

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable hydrophobic materials (for example as an emulsion in an acceptable oil) or ion exchange resins, or as sparingly soluble derivatives, for example, as a sparingly soluble salt.

The compositions are administered to a subject. A "subject" as used herein shall mean a human or vertebrate mammal including but not limited to a dog, cat, horse, cow, pig, sheep, goat, or primate, e.g., monkey. The compositions are administered in effective amounts. An effective amount of a particular agent will depend on factors such as the type of agent, the purpose for administration, the severity of disease if a disease is being treated etc. Those of skill in the art will be able to determine effective amounts.

The invention will be further more fully understood by reference to the following Examples. These Examples, however, are merely intended to illustrate the embodiments of the invention and are not to be construed to limit the scope of the invention.

EXAMPLES

Example 1

Effect of Micronization on Dissolution of Dicumarol—In vitro Effects

Materials and Methods

Dicumarol and reagent source: Dicumarol was purchased from Sigma-Aldrich (St. Louis, Mo.) and was stored at room temperature. Coulter Particle Analysis showed that the mean particle diameter was 18.5 μm based on volume statistics. All reagents and solvents used throughout were purchased from either Fisher (Pittsburg, Pa.) or Mallinckrodt (Phillipsburg, N.J.) and were of the highest grade available. Poly(fumaric-co-sebacic) anhydride synthesis: The polymer used was the polyanhydride poly(fumaric-co-sebacic) anhydride [p(FA:SA)] and was synthesized using melt polycondensation. Fumaric acid and sebacic acid monomers were purchased from Aldrich, purified in boiling ethanol, acetylated, and polymerized using melt polycondensation at 180°. A Bruker DPX300 NMR was used for ID proton NMR analysis. The polymer in deuterated chloroform was analyzed using peak ratios of the olefinic protons of the fumaric acid monomer (δ=6.91 and 6.97) and the internal aliphatic protons of the sebacic acid monomer (δ=1.32). The normalized molar ratio was determined to be FA:SA 17:83. For analysis of molecular weight, a 5% solution of p(FA:SA) in chloroform was analyzed on a Perkin Elmer LC pump model 250 gel permeation chromatography system composed of an isocratic LC pump model 250, an LC column oven model 101, an LC-30 RI detector, and a 900 series interface computer. Samples were eluted through a PL gel 5 μm mixed column and a 5 μm/50 Å column connected in series at a flow rate of 1.0 mL/min and a temperature of 40° C. The system was calibrated with a series of monodisperse polystyrene standards (MW:600–200,000) in chloroform, and the molecular weight of p(FA:SA) was found to be 12 kDa. The polymer was stored under a nitrogen purge at −20° C. until use.

Scanning Electron Microscopy: All samples were sputter-coated with an Au-Pd target for 3.5 minutes and spread out on a carbon-backed adhesive disc on top of the SEM stub. The Hitachi 2700 was used to visualize the samples at an accelerating voltage of 8 kV.

DSC: A Pyris 1 DSC with an Intercooler 2P Cooling System was used to thermally characterize the formulations. Following a baseline run at a heating and cooling rate of 10° C./min from 0 to 320° C., 5 mg samples were hermetically sealed in aluminum pans and run under a nitrogen purge using the same parameters.

Formulating Dicumarol: Particulates of dicumarol were produced through two techniques yielding different size distributions. One method was used to produce sub-micron particles, and the other produced particles with a median diameter of approximately 3 μm.

Spray-drying was used to create the 3 μm formulation. 20 g of dicumarol was dissolved in 8 L methylene chloride to make a 0.25% (w/v) solution. This solution was spray-dried in a Lab Plant SD-04 Laboratory Spraydrier using a pressure pot at a pressure of 68 psi, an atomizer pressure of 65 psi, and a solvent flow rate of 30 mL/min. The drying temperature of the inlet and outlet were 45° C. and 24° C. respectively. The spray-dried microparticles (SD) were collected off of the walls of the device, lyophilized, and stored at −20° C. until further use.

The sub-micron particulates were produced using a novel technique. 330 mg dicumarol was dissolved in 30 mL dimethylsulfoxide with a micro magnetic stir-bar rotating at 900 rpm. The temperature of the solution was raised until dissolution occurred, which was typically around 100° C. The entire volume of this solution was dispersed in 500 mL isopropyl alcohol, creating a two-phase system. After vigorous stirring, 600 mL distilled water was added in a stream resulting in a colloidal dispersion of a milky precipitate. Using a cylindrical pressure filtration apparatus, the nanoparticles were collected on 100 nm filter paper composed of mixed cellulose esters. The powder was then frozen and lyophilized for 48 hours.

To study the effect of encapsulation on the micronized drug, the polymer p(FA:SA) 17:83 was employed as a carrier and the phase inversion procedure was used to produce nanospheres. 100 mg of sub-micron dicumarol particulates was probe sonicated for 3 minutes at amplitude 35% in 20 mL methylene chloride, causing complete dissolution of the drug. 100 mg p(FA:SA) 17:83 was dissolved in this solution by sonicating for an additional 30 s. The resultant solution was dispersed into 1.0 L petroleum ether and the precipitate was collected using a 100 nm filter composed of mixed-cellulose esters. The microsphere formulation was then frozen and lyophilized for 24 hours. The dicumarol loading was determined in this formulation by a simple extraction protocol. Microspheres were incubated overnight in 2.5 N NaOH at 37° C. Upon dissolution, an aliquot of approximately 15 µg based on theoretical loading was added to 2.5 N NaOH to make a total volume of 800 µL. This mixture was agitated for 2 minutes and centrifuged for 2 minutes at 11,269 g. The supernatant was removed and analyzed on the Shimadzu UV-2501 spectrophotometer and compared to a linear standard curve of dicumarol in NaOH.

Particle Sizing: All microspheres and micronized formulations were sized using laser-light diffractometry via the Coulter Particle Size Analyzer LS 230. A 250 µg/mL suspension of microspheres in 1% pluronic F 127 [poly (ethylene oxide)-b-poly(propylene oxide)-b-poly(ethylene oxide)]/1% hydroxypropylmethylcellulose (HPMC) was introduced into the small volume fluid module. Only the Coulter output based on volume measurements was used for analysis.

In vitro Release Study: We generated release profiles for all of the formulations by incubating them in PBS Buffer (pH=7.2) at 37° C. Sink conditions were maintained by keeping the total concentration of dicumarol in water below the solubility limit, 28 µg/mL. All release studies were scaled up to 5 mg dicumarol in 180 mL PBS buffer, and each group consisted of n=4 samples. At different time points, 120 µL supernatant was obtained from each sample, placed into an Amicon Ultrafree-MC centrifugal filter device with a nominal molecular weight cutoff of 5 kDa, and centrifuged for 5 minutes at 11,269 g to remove any residual crystallized dicumarol. 100 µL of the supernatant was removed and stored at 4° C. until it was analyzed. 120 µL of fresh buffer was added back to each sample after the timepoints.

Figure 1B:
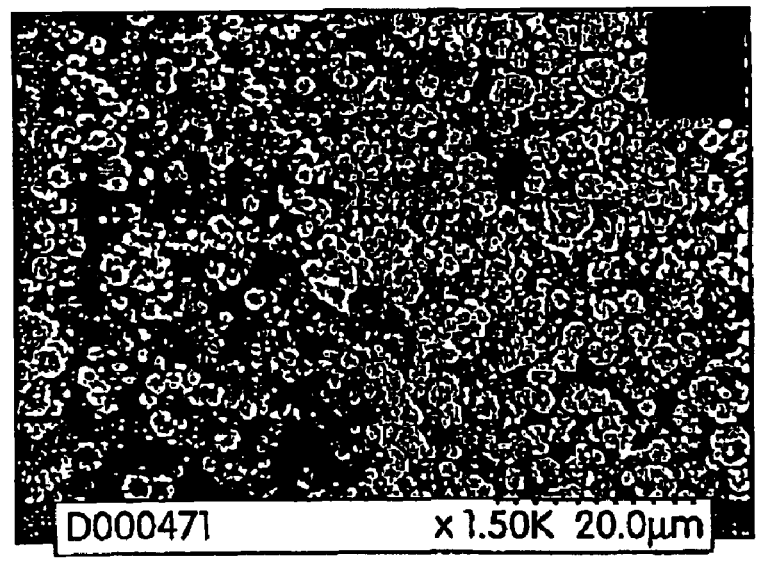
Figure 1C:
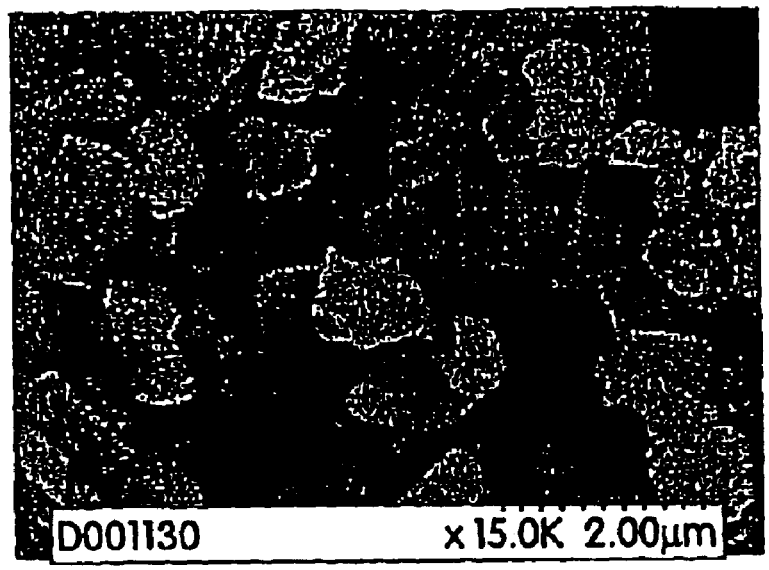
Figure 1D:
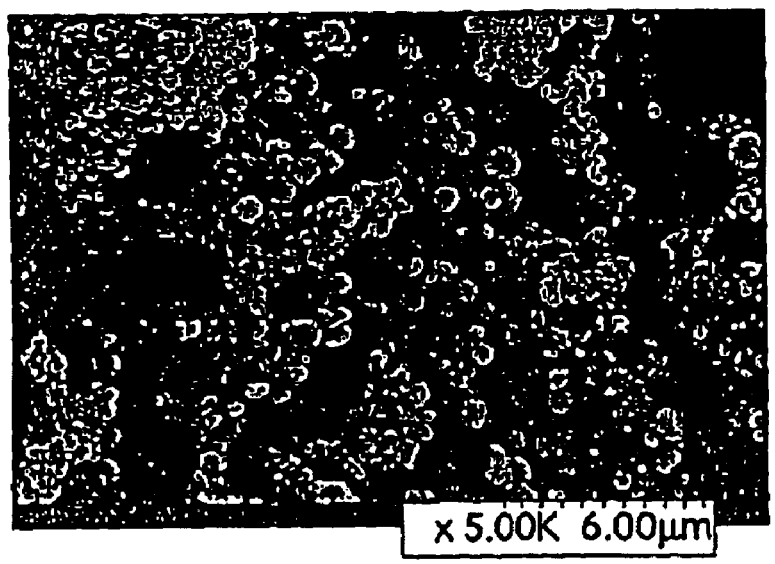

Results:

Characterization of Dicumarol Formulations: SEM micrographs of the dicumarol formulations are displayed in FIG. 1. FIG. 1A shows the stock dicumarol as supplied by Sigma (St. Louis, Mo.). The particulates were primarily in the range of 10–20 microns and have a cuboidal appearance. Spray-dried dicumarol, shown in FIG. 1B, has a round appearance and appears to be hollow. These particles were roughly 3 microns in diameter. The micronized drug is shown in FIG. 1C. This formulation in non-spherical and most of the population is in the 300 nm to 1 micron range. FIG. 1D shows the FA:SA nanospheres fabricated from the micronized formulation. Particles in this formulation were generally 1 micron in size. The loading determination of the FA:SA formulation along with the Coulter particle size data is presented in Table 1.

TABLE 1

Coulter particle size analysis of dicumarol formulations.
Data reported were generated from Coulter volume calculations.

| Formulation | Coulter Particle Analysis | | | |
| --- | --- | --- | --- | --- |
| | 25% < | 50% < | 75% < | Loading |
| Stock | 12.98 µm | 18.95 µm | 24.82 µm | 100% |
| Spray-Dried | 1.474 µm | 3.053 µm | 5.319 µm | 100% |
| Micronized | 0.433 µm | 0.535 µm | 0.701 µm | 100% |
| Encapsulated in FASA | 0.782 µm | 1.414 µm | 2.312 µm | 31% |

Figure 2:
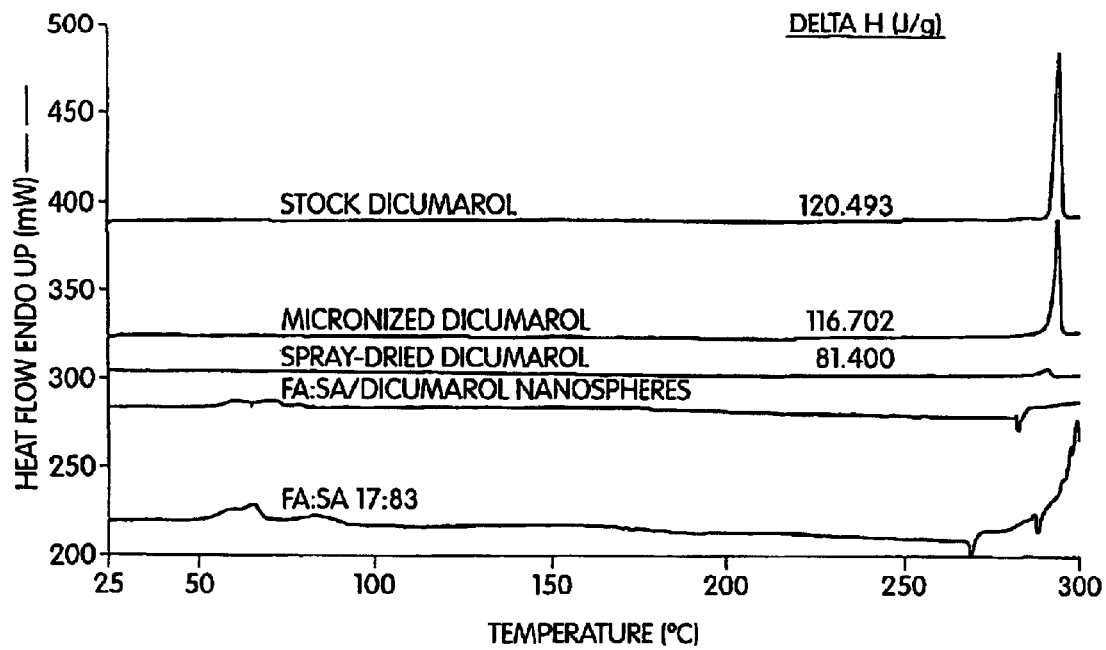
FIG. 2. DSC thermogram of dicumarol formulations.

Thermal analysis using DSC revealed the presence of a solid solution of drug in the FA:SA formulation. FIG. 2 shows the DSC thermograms of the four formulations, and for comparison, the FA:SA polymer alone. ΔH is shown on the left of each melt. The bottom curve for the blank FA:SA polyanhydride shows a variety of peaks. Between 60° C. and 90° C., the trimodal peak of the polymer melt is seen. At 275° C., the polymer and its components begin to degrade, which continues beyond 300° C. The stock dicumarol shows a distinct melt at approximately 290° C., which is consistent with the values previously reported. In the FA:SA/Dicumarol nanosphere formulation, the peak due to the melt is completely gone, indicating that a true molecular dispersion was obtained. The spray-dried and micronized formulations both show the same drug melt at about 290° C., but they have a lower ΔH than the stock dicumarol. Because the magnitude of ΔH is proportional to the relative amount of the crystalline component, the lower ΔH is probably due to the quenching of the drug solution during both of those processes, which could lead to decreased crystal growth. This process affected the crystallinity of the spray-dried formulation the most, as the ΔH was reduced by 32%. It must be noted that the melting peak in the DSC trace for the spray-dried formulation was very small because of a very small sample size. The decrease in crystallinity was not proportional to the peak area as presented, but was a function of the ΔH.

Figure 3:
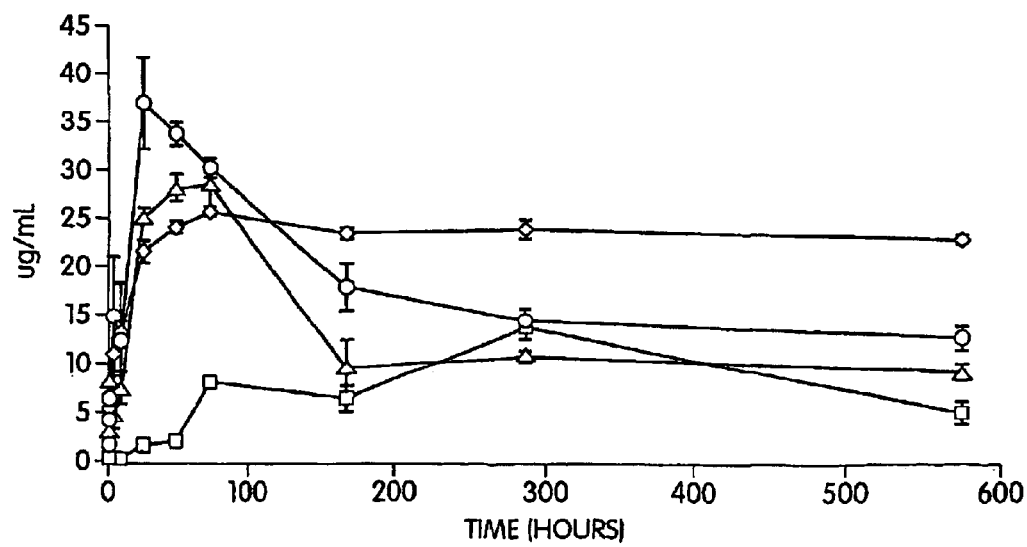
FIG. 3. In vitro dissolution curves. Micronized Dicumarol (Circles), FA:SA Encapsulated Dicumarol (Triangles), Stock Dicumarol (Diamonds), and Spray-Dried Dicumarol (Squares). Points represent mean±standard error.

The results of in vitro dissolution studies are shown in FIG. 3. Because the dissolution studies were done in a static environment, where only a small amount and not the total amount of buffer was replaced, the dissolved dicumarol was allowed to recrystallize. This led to a polymorphic state in which different populations of dicumarol were dissolved and recrystallized at different rates. In vitro, this can be seen by the increase in concentration followed by a decrease, and sometimes again followed by an increase. In vivo, however, we would not have expected to see this behavior because the dissolved dicumarol would have readily bound to plasma proteins and became metabolized.

The micronized formulation showed the most rapid dissolution, reaching a concentration of 36.9 µg/mL after only 24 hours. The dicumarol dissolved in FA:SA showed the next highest amount of dissolution, with concentrations reaching 28.8 µL after 72 hours. The time lag evident in this formulation can be attributed to the polymer coating, which degrades by surface erosion and has been used in many controlled release delivery systems. The stock dicumarol showed more of a depot effect and does not appear to recrystallize after 600 hours. The spray-dried formulation showed the lowest amount of dissolution, reaching only 13.6 µg/mL after 288 hours.

Example 2

Effect of Micronization on Relative Bioavailability of Dicumarol—In vivo Effects.

Materials and Methods

Animal Models: The following animal work was performed in accordance with the Principles of Laboratory Animal Care (NIH publication #85-23, revised 1985). Both female Yorkshire pigs and male Sprague-Dawley rats were used. Pig starting weights ranged from 15 to 20 kg, and were divided into groups of n=3, 4, or 5. The groups were kept for 12–14 weeks and were administered each formulation throughout the study. Male CD Rats weighing approximately 250 g were also used, and were divided into groups of between 8 and 12 for each study group. The rat groups were each used for only one study, and were sacrificed after the last time point.

After a fasting period of 12 hours, animals were orally gavaged with microsphere formulations suspended in a solution of 1% HPMC and 1% pluronic F127. The microsphere dose was suspended immediately prior to administration using bath sonication for 3 minutes and was administered to the stomach through a gavage tube. The suspension concentration was kept constant at 25 mg/mL, and several flushes of vehicle were administered following the dose. During administration, pigs were sedated with a combination of ketamine and medetomidine, and immediately following the procedure, the medetomidine-antagonist atipamezole was given for reversal of anesthesia. Rats were anesthetized using isoflurane gas.

A control group in each species was gavaged with blank p(FA:SA) 17:83 microspheres suspended in 1% F127/1% HPMC in order to generate a baseline for the experiment. Additionally, each species had an IV group to which we administered 25 mg/kg dicumarol dissolved in a mixture of 50% propylene glycol, 10% ethanol, and 40% 100 mM Tris at a pH of 9.0. The dicumarol was dissolved in the vehicle at a concentration of 20 mg 1 mL and administered through a chronic catheter placed in the external jugular vein of the pig. The IV dose was administered through the dorsal penile vein of the rats via a 23-gauge needle.

At specific time points, generally 0, 1, 2, 3, 5, 8, 11, 14, 25, 29, 36, 48, 60, 72, 84, and 96 hours, blood was collected from each animal. In the pig, the heparin block was removed, 1 cc of fresh blood was collected, and another 1.5 cc heparin solution was added to the catheter. 300 $\mu$L of rat blood was sampled from the tail vein. The blood samples were collected in heparinized 1.5 mL siliconized microfuge tubes and centrifuged for 5 minutes at 11,269 g. Approximately 200 $\mu$L plasma was removed and stored at 4° C. prior to being analyzed.

Dicumarol Quantification: A double extraction technique with slight modifications was employed. A 50 $\mu$L sample of the plasma in a 15 mL Falcon tube was first acidified with 300 $\mu$L of a citrate/phosphate buffer with pH-3.0 by shaking and allowing the mixture to interact for 5 minutes. Next, the dicumarol was extracted from the plasma by adding 3 mL heptane and rotating each sample end over end for 10 minutes. The tubes were centrifuged for 5 minutes at 3000 rpm and the top heptane layer was separated and put into a new tube. Next, 1 mL of 2.5 N NaOH was added to each tube and the mixture was again rotated end over end for 10 minutes. Following centrifugation at 3000 rpm for 5 minutes, the aqueous phase was removed and the absorbance was read at 315 nm on a Shimadzu UV-2501 spectrophotometer. A standard curve for this assay was obtained by doping plasma obtained from control animals with known amounts of dicumarol in sodium hydroxide.

Bioactivity: Plasma samples taken at the $T_{max}$ were tested for drug activity using the prothrombin time test (PTT) performed by IDEXX Veterinary Services in North Grafton, MA. Plasma was collected and submitted for testing in tubes coated with citrate.

Statistics and Pharmacokinetic Analysis: Standard errors were calculated and t-tests were performed using Microsoft Excel. T-tests were employed to compare the plasma curves generated from the different formulations, and p was calculated using AUCs normalized by dose. AUC, $C_{max}$, and $T_{max}$ were all calculated from the Graphpad Prism Software. Non-compartmental pharmacokinetics were assumed.

Results

In vivo Studies: Bioactivity tested positive using the prothrombin time test. Samples taken from plasma corresponding to the $C_{max}$ all showed clotting times longer than 90 seconds, compared to 12 to 17 seconds in normal animals.

Figure 4:
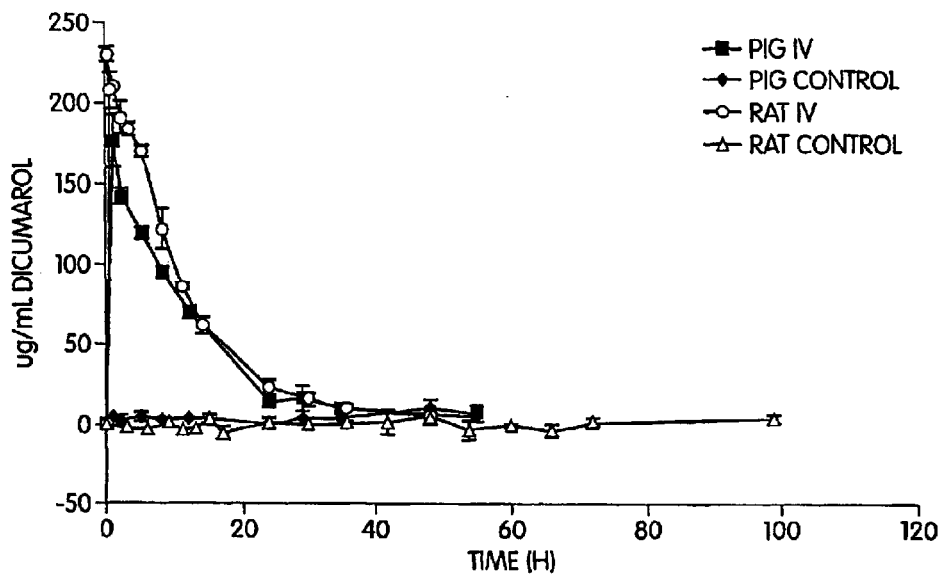
FIG. 4. Pig and rat control curves. IV [pig] (Squares), IV [rat] (Circles), Blank FA:SA Microspheres [pig] (Diamonds), and Blank FA:SA Microspheres [rat] (Triangles). Points represent mean±standard error.

FIG. 4 shows the control curves, including the IV bolus injection and oral delivery of blank FA:SA nanospheres to both the rat and pig. The IV curves both peaked very rapidly and showed only a downward slope indicating elimination. The rats received 24.0 mg/kg while the pigs received 24.4 mg/kg. The IV dose was administered in a vehicle, which consisted of 50% propylene glycol, 40% Tris base, and 10% ethanol. This mixture, although used frequently as an IV vehicle, has the potential to disrupt normal physiology due to its hyperviscosity and pH. The blank microsphere curves serve as proof for the negligible interference of p(FA:SA) with the detection of dicumarol, as both curves for the rat and pig were extremely low and fluctuated within about 5 mg/mL of the baseline.

Drug formulations were administered to animals at a dose of 25 mg/kg. The p(FA:SA) nanospheres, however, were fed at a lower dose due to difficulty determining dicumarol loading early in the experiment. Because of this, the amplitude of the plasma curves cannot be compared directly with the other formulations in FIG. 5; only the profile can be analyzed, including $T_{max}$. The only comparisons that can be made were based on relative bioavailability calculated from area under the curve and dose administered which is presented later in table 2.

Figure 5:
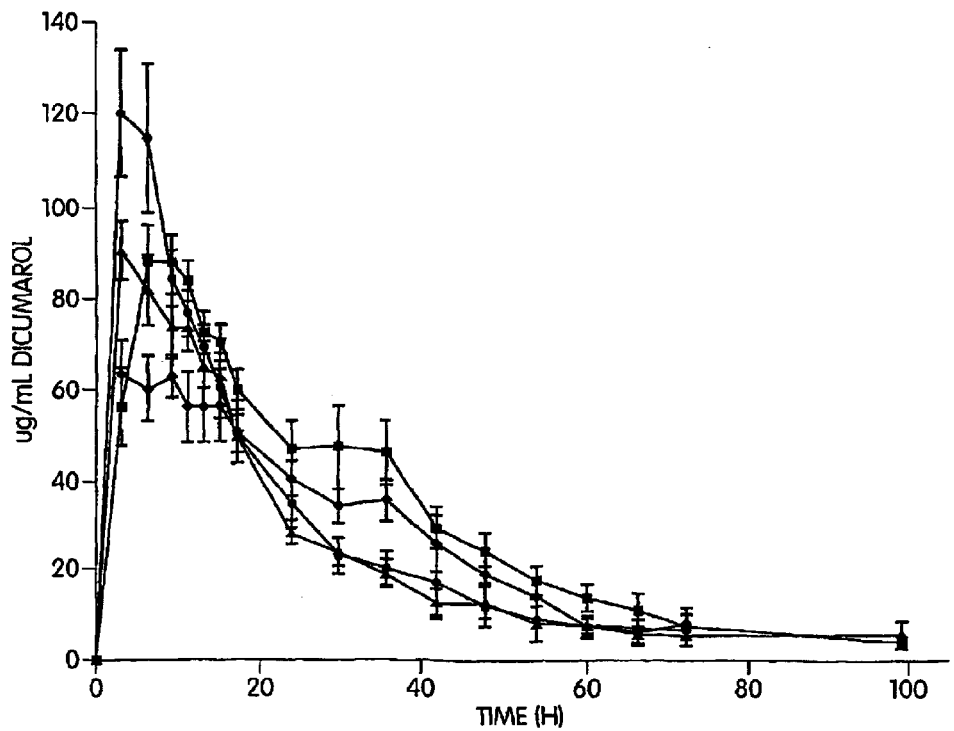
FIG. 5. Plasma curves in the rat after oral administration, Micronized Dicumarol (Circles), Spray-Dried Dicumarol (Triangles), FA:SA Dicumarol Nanospheres (Squares), and Stock Dicumarol (Diamonds). Points represent mean± standard error.

FIG. 5 shows the plasma curves generated from the rat experiments. All doses were 25 mg/kg except for the p(FA:SA) formulation, which is 18.2 mg/kg. The micronized drug showed the highest absorption, reaching 120 $\mu$g/mL after only 3 hours, followed by a continuous decrease until 60 hours. The next highest concentration was achieved by the spray-dried dicumarol particles, which reached 90 $\mu$g/mL after 3 hours and declined very rapidly within the next 30 hours. The FA:SA nanosphere formulation showed excellent absorption, with relatively high concentrations in the blood until 60 hours. This formulation reached 88 $\mu$g/mL after 6 hours, decreasing to 47 $\mu$g/mL after 24 hours, where it stayed for an additional 12 hours. The stock dicumarol showed the lowest levels of absorption, reaching 64 $\mu$g/mL after 3 hours and decreasing significantly after 15 hours.

Figure 6:
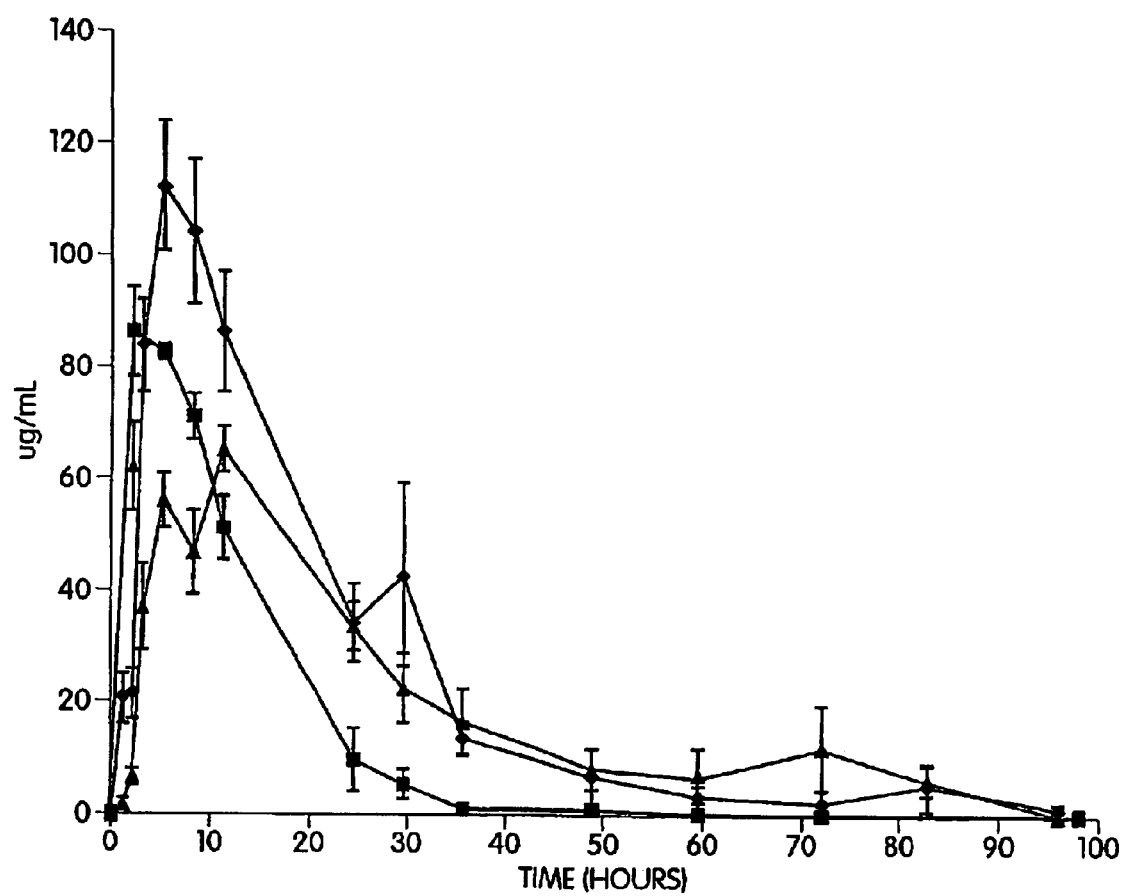
FIG. 6. Plasma curves in the pig after oral feeding of Spray-Dried Dicumarol (Squares), Micronized Drug (Diamonds), and FA:SA Dicumarol Nanospheres (Triangles). Points represent mean±standard error.

Results in the pig were very similar to those from the rat (FIG. 6). Again, all doses were 25 mg/kg except for the FA:SA formulation, which was 18.2 mg/kg. The micronized drug shows very good absorption, reaching 112 $\mu$g/mL after 5 hours, and showing a second peak at 30 hours. The FA:SA formulation showed a more prolonged absorption, with high concentrations extending to 30 hours. The spray-dried dicumarol peaked at 2 hours at a concentration of 86 $\mu$g/mL and rapidly decreased by 24 hours. In both rats and pigs, it was clear that the micronized drug and FA:SA formulation offered an advantage over the slightly amorphous spray-dried formulation and the stock dicumarol. Pharmacokinetic analysis was used to more accurately compare the formulations and to draw conclusions based on both the animal model as well as the characteristics of the formulation.

Pharmacokinetic calculations are presented in Table 2. In both cases, the FA:SA nanosphere formulation showed the highest relative bioavailability, with 132% in the rat and 114% in the pig. The polymer's ability to control the release and absorption was also reflected by these results. Within each species, $C_{max}$ was among the lowest and $T_{max}$ was the highest in the p(FA:SA) formulation. Because this system was a solid solution, the dissolution of the drug was totally dependent upon the degradation of the polymer, which in this case was a relatively slow surface degrading mechanism. The micronized drug also showed improved relative bioavailability over other formulations, with 100% in the rat and 101% in the pig. But control of dissolution afforded by the polymer was lost, evidenced by the increase in $C_{max}$ and decrease in $T_{max}$ in both species. The semi-amorphous spray-dried dicumarol formulation showed the worst absorption, with only 85% in the rat and 58% in the pig. $C_{max}$ and $T_{max}$ were intermediate between the micronized and FA:SA formulations in both the rat and pig.

TABLE 2

Pharmacokinetic calculations.

| Formulation | Dose (mg/kg) | $C_{max}$ (μg/mL) | $T_{max}$ (hours) | AUC (μg-hour/ml) | Relative Bioavailability |
|---|---|---|---|---|---|
| RAT MODEL | | | | | |
| IV Bolus | 25 | 129 ± 10.0 | 3 ± 0.0 | 2625 ± 143 | 100 ± 0.0% |
| Stock | 25 | 73 ± 6.0 | 14 ± 2.0 | 2666 ± 206 | 90.1 ± 7.3% |
| Spray-Dried | 25 | 100 ± 6.0 | 7 ± 1.0 | 2238 ± 109 | 85.3 ± 4.2% |
| Micronized Drug | 25 | 144 ± 13.0 | 4.2 ± 0.7 | 2624 ± 233 | 100.0 ± 9.1% |
| FA:SA Nanospheres | 18.2 | 75 ± 7.7 | 21.1 ± 7.5 | 2535 ± 157 | 132.6 ± 10.7% |
| PIG MODEL | | | | | |
| IV Bolus | 24 | 178 ± 16.5 | 1.0 ± 0.0 | 2116 ± 155 | 100 ± 0.0% |
| Spray-Dried | 25 | 91 ± 5.0 | 2.8 ± 0.8 | 1283 ± 102 | 58.2 ± 7.5% |
| Micronized Drug | 25 | 117 ± 13.1 | 6.5 ± 0.9 | 2366 ± 407 | 100.9 ± 8.9% |
| FA:SA Nanospheres | 18.2 | 67 ± 3.4 | 10.4 ± 0.6 | 1848 ± 164 | 113.8 ± 14.6% |

Statistical analysis of the pharmacokinetic data was performed in order to compare the spray-dried, micronized, and FA:SA nanosphere dicumarol formulations. Two-tailed t-tests were used to compare AUCs, and in the case of the FA:SA formulation, AUCs were normalized by dose to account for the difference. In all cases where sample populations differ, unequal variance was assumed. In the rat model, the FA:SA nanosphere formulation was statistically different from the other formulations with $p<0.03$ in all cases. In the pig both the FA:SA formulation and micronized drug were significantly different from the spray dried dicumarol, with $p<0.05$ in both cases.

Example 3

Effect of Micronization and Incorporation of a Bioadhesive Polymer on the Dissolution of Dicumarol—In vitro Effects.

Materials and Methods

Dicumarol and Reagent Source and methods for Poly (fumaric-co-sebacic) anhydride synthesis, Scanning Electron Microscopy and formulating dicumarol were described in Example 1

The dicumarol formulation will be referred to throughout this Example and Example 4 as micronized drug with adhesive polymer, or MDAP. P(FA:SA) was used in this process because it was found to prevent aggregation, both in the micronization process as well as in suspension.

NMR: A Bruker DPX300 NMR was used for ID proton NMR analysis. The polymer in deuterated chloroform was analyzed using peak ratios of the olefinic protons of the fumaric acid monomer ($\delta=6.91$ and 6.97) and the internal aliphatic protons of the sebacic acid monomer ($\delta=1.32$). The normalized molar ratio is determined to be FA:SA 17:83.

GPC: For analysis of molecular weight, a 5% solution of p(FA:SA) in chloroform was analyzed on a Perkin Elmer LC pump model 250 gel permeation chromatography system composed of an isocratic LC pump model 250, an LC column oven model 101, an LC-30 RI detector, and a 900 series interface computer. Samples were eluted through a PL gel 5 μm mixed column and a 5 μm/50 Åcolumn connected in series at a flow rate of 1.0 mL/min and a temperature of 40° C. The system was calibrated with a series of monodisperse polystyrene standards (MW: 600–200,000) in chloroform, and the molecular weight of p(FA:SA) was 12 kDa. The polymer was stored under a nitrogen purge at $-20°$ C. until use.

Microencapsulation: Using different fabrication techniques, microsphere characteristics were varied based on formulation parameters including size and bioadhesiveness. These two parameters were key to the enhancement of relative bioavailability, and it is our aim to fabricate enough formulations to differentiate their relative importance. All formulations were frozen, lyophilized for at least 24 hours, and kept at $-20°$ C. until use.

The micronized formulations discussed previously were fed by themselves orally to pigs. Additionally, these formulations were encapsulated in different size distributions and polymer compositions using the phase inversion technique. This resulted in solid solutions within their respective polymer carriers.

The phase inversion procedure was used to produce nano- and microspheres. 666 mg spray-dried dicumarol was probe sonicated for 3 minutes at amplitude 35% in 25 mL methylene chloride. 1.0 g p(FA:SA) 17:83 was added to this and sonicated for an additional 30 s. The resultant solution (4% w/v p(FA:SA)) containing dicumarol microparticulates was dispersed into 1.0 L petroleum ether and the precipitate was collected using either a 100 or 220 nm filter. The microsphere formulation was then frozen and lyophilized for 24 hours. We will refer to this formulation as adhesive microspheres (AM). Another formulation was fabricated using the same technique but encapsulating the MDAP micronized drug. We will refer to this formulation as adhesive nanospheres (AN).

A non-adhesive formulation was made from poly(lactic acid) (PLA) with a molecular weight of 24 kDa using the same technique and encapsulating the MDAP micronized drug. This formulation will be referred to as nonadhesive nanospheres (NN).

The dicumarol loading was determined in all formulations by a simple extraction protocol. Microspheres were incubated overnight in 2.5 N NaOH at 37° C. Upon dissolution, an aliquot of approximately 15 μg based on theoretical loading was added to 2.5 N NaOH to make a total volume of 800 μL. This mixture was agitated for 2 minutes and centrifuged for 2 minutes at 11,269 g. The supernatant was removed and analyzed on the Shimadzu UV-2501 spectrophotometer and compared to a linear standard curve of dicumarol in NaOH.

Due to the size of the animal model, we scaled up our fabrication process. Because the initial solvent ratios were crucial for reproducibility, we maintained the conditions for this step as previously described. 10 batches were fabricated simultaneously, and they were combined into a pressure pot for filtration. The precipitate in petroleum ether was passed through a 293 mm wide plate filter made by Millipore® with a pore size of either 100 or 220 nm depending on the formulation.

Particle Sizing: All microspheres and micronized formulations were sized using laser-light scattering via the Coulter Particle Size Analyzer LS 230. A 250 µg/mL suspension of microspheres in 1% pluronic F127 [poly(ethylene oxide)-b-poly(propylene oxide)-b-poly(ethylene oxide)]/1% hydroxypropylmethylcellulose (HPMC) was introduced into the small volume fluid module. Only the Coulter output based on volume measurements was used for analysis.

In vitro Release Study: We generated release profiles for all of the formulations by incubating them in PBS Buffer (pH=7.2) at 37° C. Sink conditions were maintained by keeping the total concentration of dicumarol in water below the solubility limit, 28 µg/ml. All release studies were scaled up to 5 mg dicumarol in 180 mL PBS buffer, and each group consisted of n=4 samples. At different time points, 120 µL supernatant was obtained from each sample, placed into an Amicon Ultrafree-MC centrifugal filter device with a nominal molecular weight cutoff of 5 kDa, and centrifuged for 5 minutes at 11,269 g to remove any residual crystallized dicumarol. 100 µL of the supernatant was removed and stored at 4° C. until it was analyzed. This amount was replenished with fresh buffer.

Results

Figure 7A:
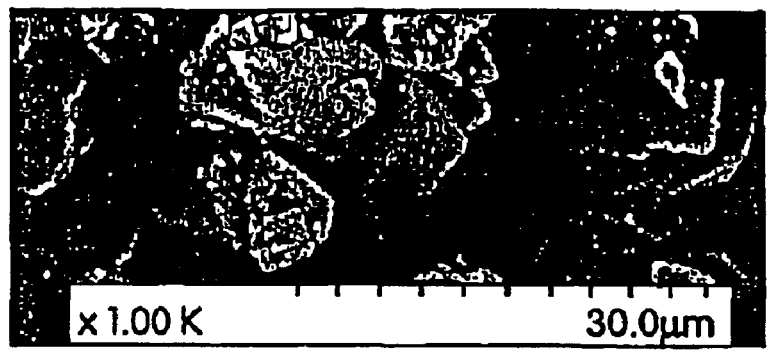
FIG. 7. SEM micrographs of dicumarol formulations. (A) Stock dicumarol, (B) Micronized Dicumarol with FA:SA [MDAP], (C) Spray-Dried [SD], (D) Phase-Inverted Spray-Dried with FA:SA [AM], (E) Encapsulation of B with p(FA:SA) using phase inversion microencapsulation FA:SA [AN], and (F) Phase-Inverted Spray-Dried with PLA [NN].
Figure 7B:
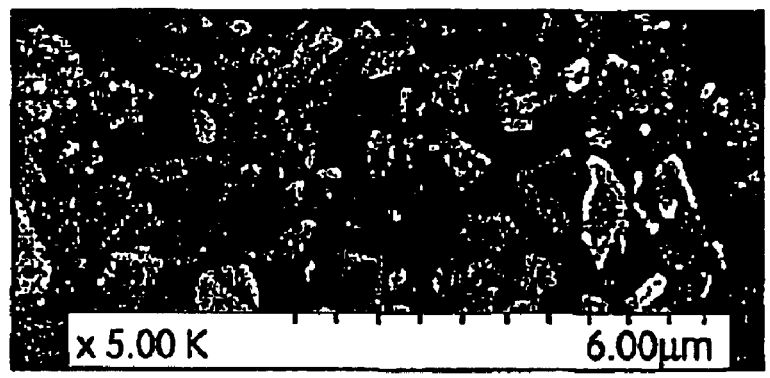
Figure 7C:
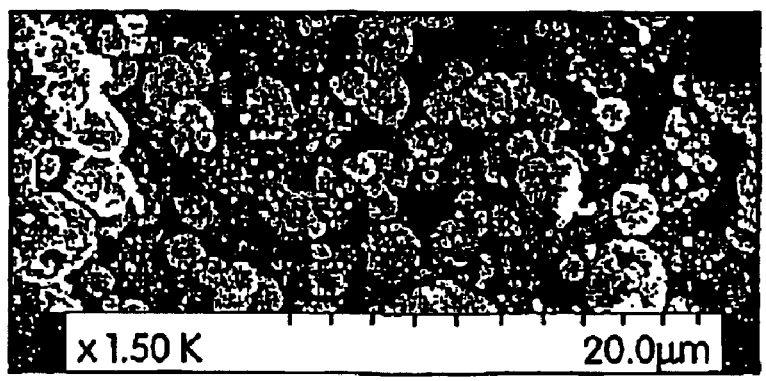
Figure 7D:
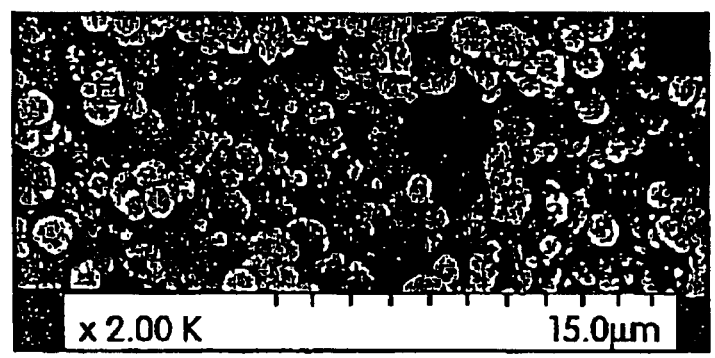
Figure 7E:
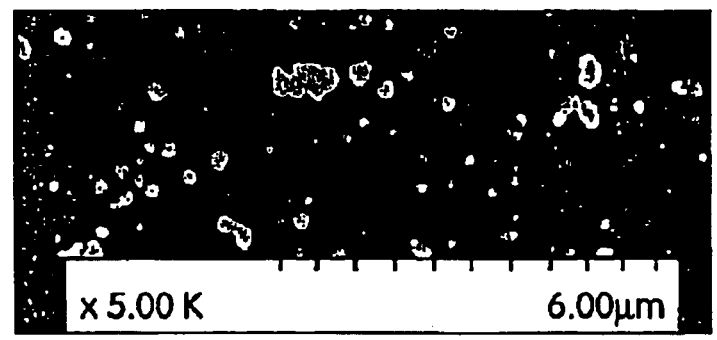
Figure 7F:
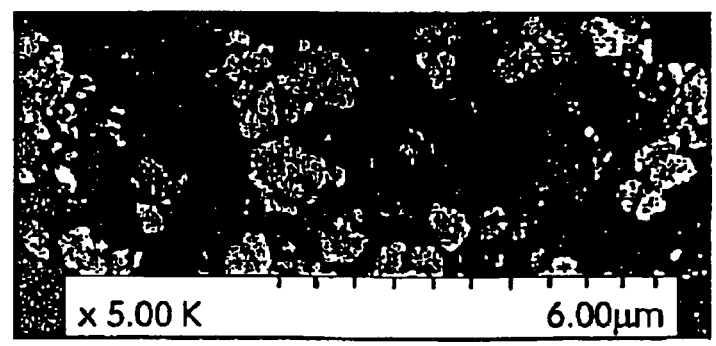

Formulation Characterization: SEM analysis revealed very different morphologies of the various formulations (FIG. 7). The stock dicumarol is shown in FIG. 7A to illustrate the dissimilar appearance compared to the formulations prepared for these experiments. It has a very blocky structure with smooth surfaces, and is approximately 25 µm in size. The spray-dried formulation (SD) show a morphology resembling hollow and solid spheres with a small amount of nanoprecipitate on the surface (FIG. 7B). It is much smaller than the stock dicumarol. The micronized drug with 7% p(FA:SA) (MDAP) is much smaller in size than the spray-dried and stock dicumarol, and retained the somewhat blocky appearance of the original drug particles (FIG. 7C). This population of particles also appeared to be very monodisperse. The microspheres obtained by encapsulating the spray-dried drug in p(FA:SA) (AM) showed a very porous structure, were somewhat uniform in size, and were not aggregated (FIG. 7D). The p(FA:SA) microspheres encapsulating the dissolved MDAP formulation (AN) had a much more spherical shape than the micronized formulation from which it was made and were just slightly larger in size (FIG. 7E). The polymer coating also appears to have a porous structure. The non-adhesive poly(lactic acid) formulation (NN) fabricated with the MDAP formulation were extremely small and showed evidence of encapsulation based on the uniform morphology of the microsphere population (FIG. 7F).

Coulter particle size analysis revealed quantitatively the differences seen in the SEM micrographs. The results are presented in Table 3, along with a description of each formulation and the abbreviation we were using to describe it. The volume statistics can be found corresponding to each formulation, and the data are displayed as the percent of the population less than the size listed. Analysis of the data for the 50 percentile showed that the MDAP micronized drug made from the novel process described earlier and the formulations incorporating it, AN and NN, were much smaller than the spray-dried formulations.

Drug loading determined by NaOH extraction was also presented in Table 3. The encapsulated formulations containing polymer ranged from 31% to 40% loading, which is a function of the relative solubility of the polymer and drug within the encapsulation process. MDAP was found to be composed of 93% dicumarol, so this formulation will be considered a micronized drug with a small amount of bioadhesive enhancer.

TABLE 3

Formulation parameters and size information.
Coulter data is based on volume measurements.

| Formulation Name | Composition | Coulter Sizing Information | | | Drug Loading |
|---|---|---|---|---|---|
| | | 25% < | 50% < | 75% < | |
| SD | Spray-Dried microparticulates | 1.474 µm | 3.053 µm | 5.319 µm | 100% |
| MDAP | Micronized dicumarol with 7% adhesive polymer | 0.415 µm | 0.525 µm | 0.612 µm | 93% |
| AM | Adhesive microspheres (p(FA:SA) 17:83 microspheres with dicumarol particulates) | 1.421 µm | 3.533 µm | 8.208 µm | 40% |
| AN | Adhesive nanospheres (p(FA:SA) 17:83 nanospheres with homogenous drug dispersion) | 0.782 µm | 1.414 µm | 2.312 µm | 31% |
| NN | Nonadhesive nanospheres (PLA nanospheres with homogenous drug dispersion) | 0.478 µm | 0.552 µm | 0.650 µm | 39% |

Figure 8:
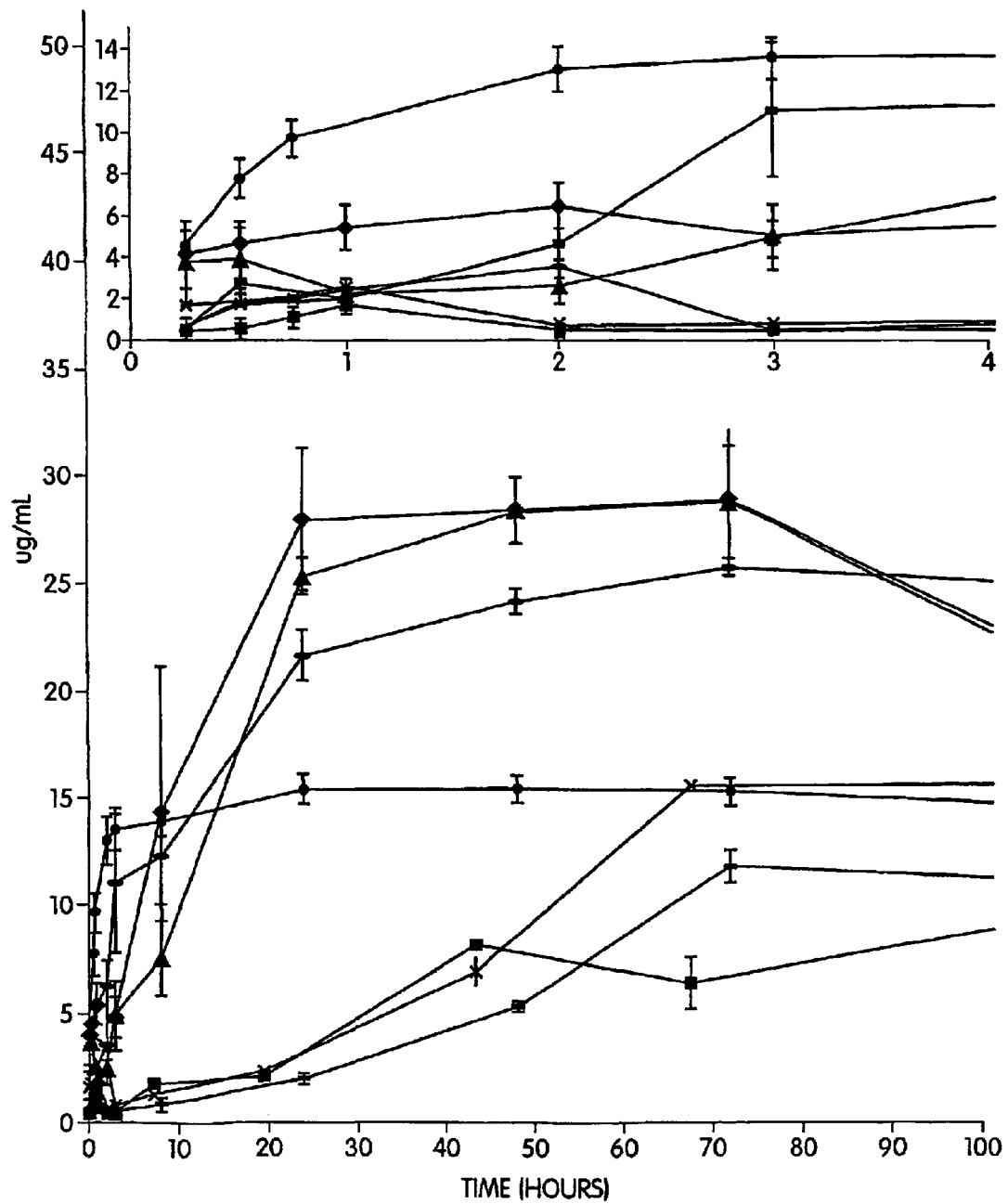
FIG. 8. In vitro dissolution and release studies of dicumarol formulations. The top inset shows the first 4 hours. Micronized Dicumarol with p(FA:SA) (MDAP) (diamonds), Encapsulation of MDAP with p(FA:SA) (AN) (triangles), Encapsulation of Spray-Dried Dicumarol with p(FA:SA) (AM) (X), Spray-Dried Dicumarol (SD) (squares), Encapsulation of MDAP with poly(lactic)acid (circles), Encapsulation of SD in p(FA:SA) using Solvent Removal Technique (–), Stock Dicumarol (+).Points represent mean±standard error.

The general nature of the in vitro dissolution and release curves for each formulation was one of sporadic dissolution and recrystallization (FIG. 8). This was seen by the increasing concentration followed by a lower concentration, sometimes again followed by another increase. This dynamic process is due to the hydrophobicity of the drug and other thermodynamic considerations. Presumably, as the micronized drug was dissolved, a certain population in solution was already recrystallizing into another population of solid particles, which were larger than the original formulation because of the slower rate at which crystallization occurs at 37° C. in buffer compared to the conditions of the fabrication process. These large particles then underwent another round of dissolution, which was much slower and was occurring simultaneously with the dissolution of another population of micronized particles from the original formulation. Only the first 100 hours of the in vitro dissolution curves are presented here in order to compare these curves to the in vivo plasma curves, which terminate at 96 hours.

Overall, the particles made from MDAP showed a much more pronounced dissolution than the formulations made with the spray-dried dicumarol. Both MDAP and AN showed a very nice correlation between the amount of drug in solution and the amount of p(FA:SA) in the formulation. The curves were staggered based on drug loading, with the MDAP formulation with 93% dicumarol loading showing the highest amount of dissolution, and AN with 31% loading showing slightly less. The NN microspheres showed a much slower and controlled dissolution; probably because of the hydrophobic nature of the highly crystalline 24 kDa poly (lactic acid) used to encapsulate the drug. The larger spray-dried formulations, AM and SD, both showed extremely low levels of dissolution, and in both cases, concentrations did not rise to comparable levels until 8 hours. This resembled more of a depot effect than the encapsulated micronized formulations.

Example 4

Effect of Micronization and Incorporation of a Bioadhesive Polymer on the Relative Bioavailability of Dicumarol—In vivo Effects Animal Model: The following animal work was performed in accordance with the Principles of Laboratory Animal Care (NIH publication #85-23, revised 1985). Female Yorkshire pigs were used throughout the study, with starting weights ranging from 15 to 20 kg, and were divided into groups of n=3, 4, or 5 depending on availability. The groups were kept for 12–14 weeks and were administered each formulation throughout the study.

Following a 2-week acclimation period, catheters were surgically implanted into the external jugular vein of each of the pigs. Under isoflurane anesthesia, an incision from just cranial to the sternum to a point just caudal of the angle of the jaw was made. Using blunt dissection, a section of the external jugular vein was isolated. A Swan Ganz catheter was then fed through a subcutaneous tunnel starting between the shoulders to the point of the isolated jugular vein. A small incision was made in the vein and the catheter was advanced towards the atrium until arrhythmia. At this point, the catheter was retracted 3 cm distally and was anchored to the surrounding tissues. The catheter was tested for patency and flow, blocked with heparin, and the wound was closed. The length of the catheter exiting from between the shoulders was coiled up and stored within a protective jacket placed on each animal.

After a fasting period of 12 hours, animals were orally gavaged with microsphere formulations suspended in a solution of 1% HPMC and 1% pluronic F127. The microsphere dose was suspended immediately prior to administration using bath sonication for 3 minutes and was administered to the stomach through a gavage tube placed with the aid of a laryngoscope. The suspension concentration was kept constant at 50 mg/mL, and several flushes of vehicle were administered following the dose. For most groups, the dose given was approximately 25 mg/kg, and several study groups were given either 5 mg/kg or 15 mg/kg dicumarol to investigate the dose response of 2 of the micronized formulations containing polymer. During administration, animals were sedated with a combination of ketamine and medetomidine, and immediately following the procedure, the medetomidine-antagonist atipamezole was given for reversal of anesthesia.

A control group was gavaged with blank p(FA:SA) 17:83 microspheres suspended in 1% F127/1% HPMC in order to generate a baseline for the experiment. Additionally studied was an IV group to which we administered 25 mg/kg dicumarol dissolved in a mixture of 50% propylene glycol, 10% ethanol, and 40% 100 mM Tris at a pH of 9.0. The dicumarol was dissolved in the vehicle at a concentration of 20 mg/mL and administered through the catheter over a period of 5 minutes.

At specific time points, generally 0, 1, 2, 3, 5, 8, 11, 14, 25, 29, 36, 48, 60, 72, 84, and 96 hours, blood was collected from each animal. The heparin block was removed, 1 cc of fresh blood was collected, and another 1.5 cc heparin solution was added to the catheter. The blood samples were collected in heparinized 1.5 mL siliconized microfuge tubes and centrifuged for 5 minutes at 11,269 g. Approximately 500 $\mu$L plasma was removed and stored at 4° C. prior to being analyzed.

Methods for Dicumarol Quantification, Bioactivity Assays, and Statistics and Pharmacokinetic Analysis were described in Example 2.

Results of in vivo Studies

Figure 9:
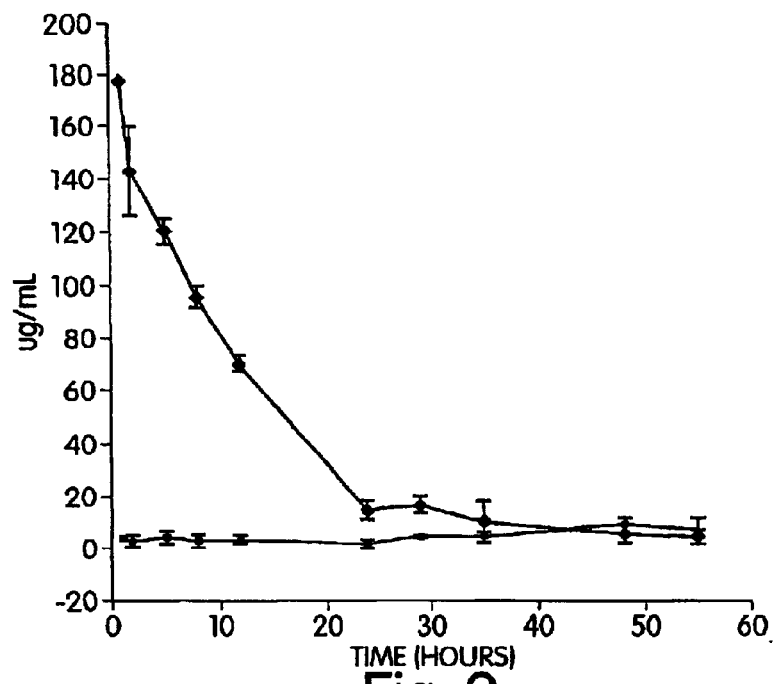
FIG. 9. In vivo control curves in the pig. IV administration (Diamonds), Blank p(FA:SA) microspheres (Squares).

Control Curves: The IV curve was as expected, with a very sharp peak followed by a rapid decline in plasma levels (FIG. 9). The majority of the drug was absorbed in the first 24 hours.

Figure 10:
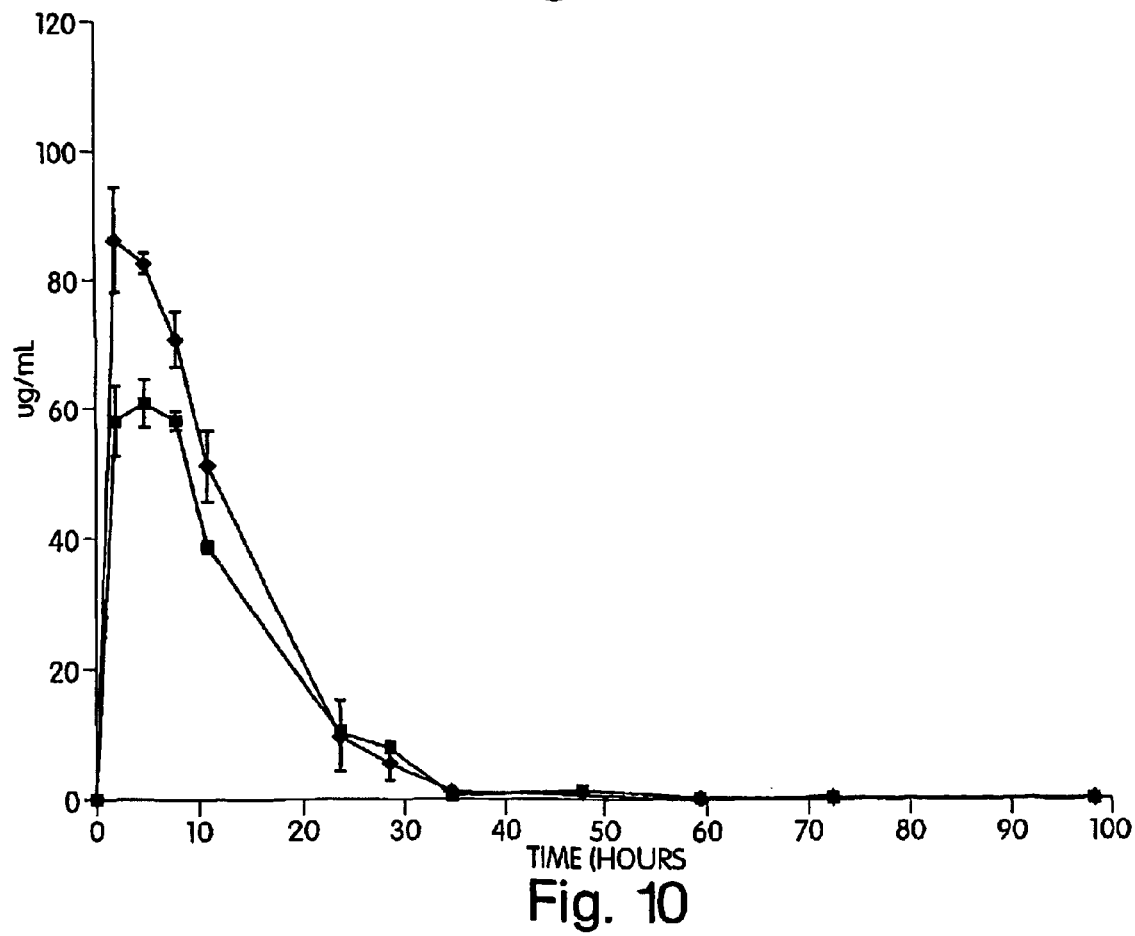
FIG. 10. Plasma curves from study groups administered with spray-dried formulations. SD (diamonds), AM (squares). Points represent mean± standard error.

Spray-dried Formulations: Both SD and AM formulations were fed at a dose of 25 mg/kg dicumarol, thus the dose for the AM formulation and for all other formulations containing polymer are scaled up because the loading was less than 100%. The plasma curves are shown in FIG. 10. Both of the formulations showed an obvious decrease in the concentration achieved compared to the IV curve in FIG. 9. They offered a small amount of elongation of absorption, but were overall much less pronounced. Between the two formulations, SD showed an improvement over the encapsulated formulation, which also declined to zero just after 30 hours.

Micronized Formulations: We attempted to maintain a standard dose of 25 mg/kg dicumarol throughout these experiments. However, due to the difficulty in determining the loading at the onset of the study, three of the formulations were fed a different dose, with AN receiving 18.2 mg/kg, NN receiving 30.6 mg/kg, and MDAP receiving 23.0 mg/kg. For this reason, the plasma curves for these three formulations could not be directly compared to each other or any of the other curves. They can, however, be compared when calculating relative bioavailability, because it is normalized by dose. Additionally, statistical analysis using a t-test also necessitated normalization by dose received.

Figure 11:
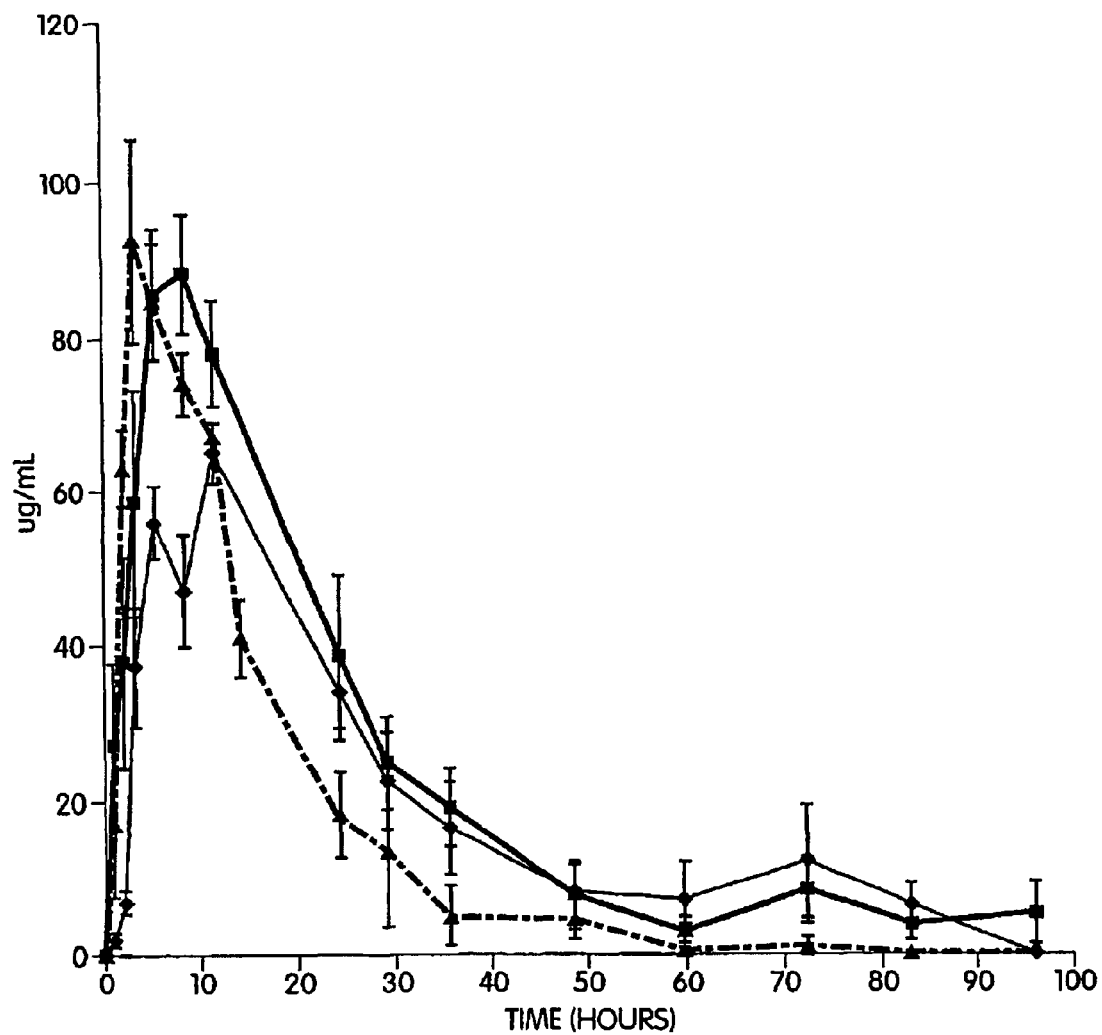
FIG. 11. Plasma curves from pigs fed with micronized formulations. Doses are as follows: (MDAP) 23.0 mg/kg, (AN) 18.2 mg/kg, and (NN) 30.6 mg/kg. MDAP (squares), (AN) diamonds, NN (triangles). Points represent mean±standard error.

The plasma curves from the studies using the formulations with micronized drug are shown in FIG. 11. Compared to the absorption of the spray-dried formulations, the overall magnitude of absorption for these curves was elevated. The curves in FIG. 11 were very similar in shape, except for the NN formulation, which showed an early peak with very low levels of absorption in the later time points. Because the doses given were not the same, only the curve profiles can be compared, and not the magnitude. All of the micronized formulations showed relatively high concentrations in the blood up until 60 hours, compared to only 30 hours with the spray-dried formulations.

Figure 12:
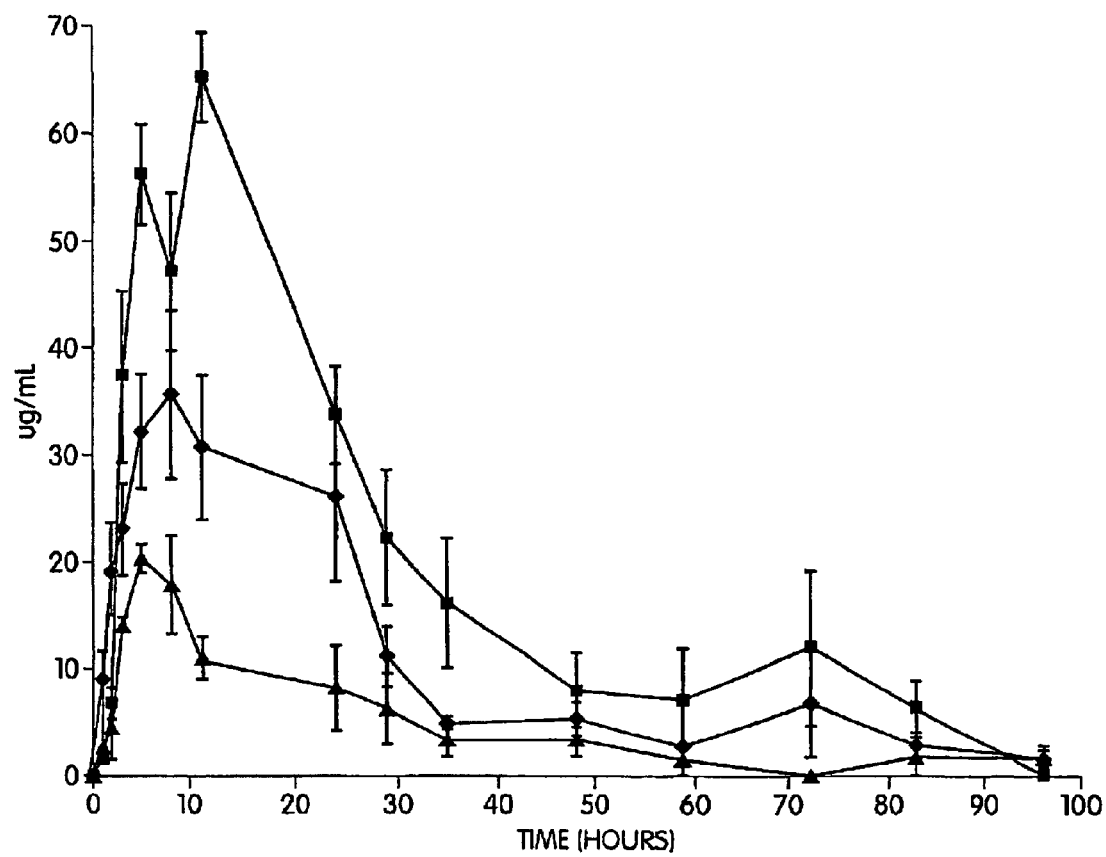
FIG. 12. Dose escalation of AN formulation. AN 3.6 mg/kg (triangles), AN 10.9 mg/kg (diamonds), AN 18.2 mg/kg (squares). Points represent mean±standard error.
Figure 13:
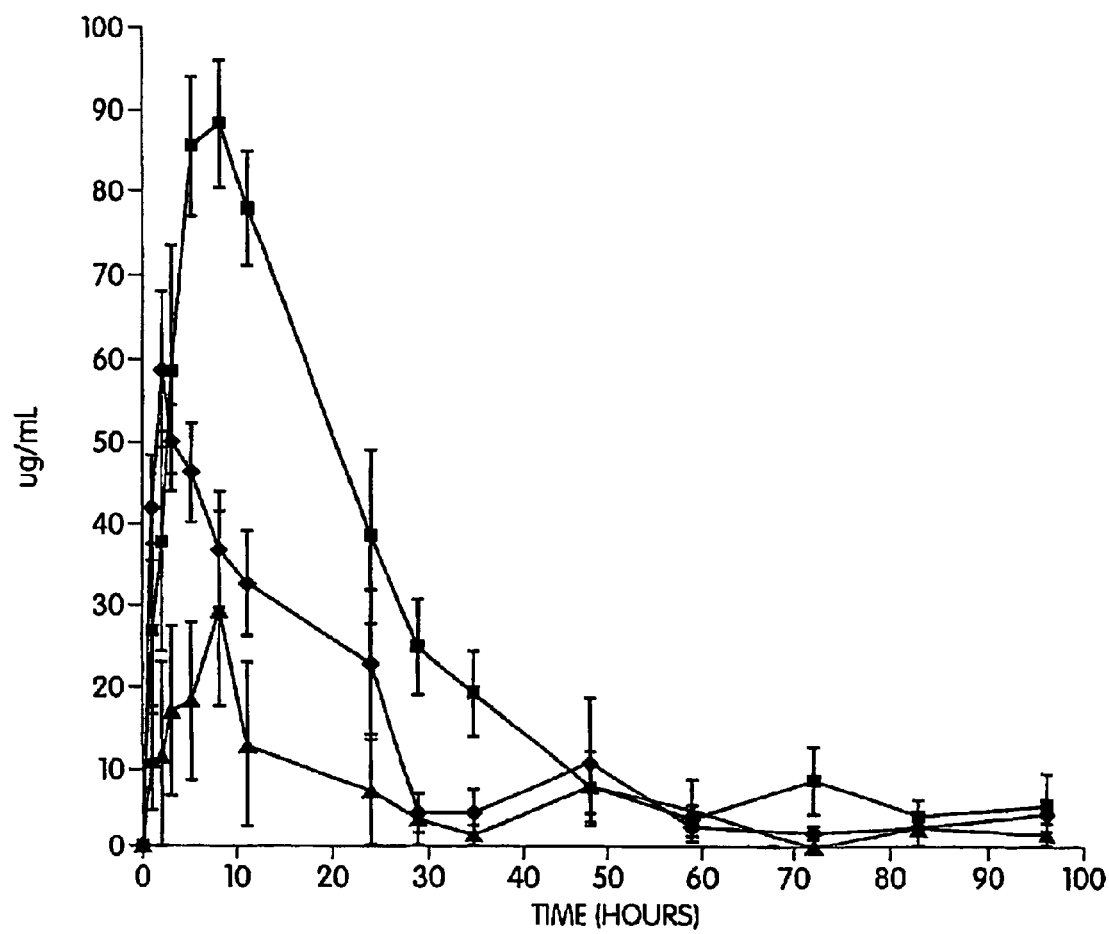
FIG. 13. Dose escalation of MDAP formulation. MDAP 5 mg/kg (triangles), MDAP 15 mg/kg (diamonds), MDAP 23 mg/kg (squares). Points represent mean±standard error.

The dose escalation curves were shown in FIGS. 12 and 13. Doses for the AN formulation were 3.6 mg/kg, 10.9 mg/kg, and 18.2 mg/kg. Animals dosed with MDAP were fed doses of 5 mg/kg, 15 mg/kg, and 23 mg/kg. The AN curves in FIG. 12 show elevated plasma levels for each increase in dose, and the time at which the concentration is the highest, $T_{max}$, is also greater for each increasing dose. MDAP curves show similar results, with each dose increasing the overall plasma levels significantly, except that the $T_{max}$ shows no distinctive pattern.

Pharmacokinetic Analysis: The effect of the formulations in this study can be compared by calculating the pharmacokinetic parameters: relative bioavailability (BA), $C_{max}$, and $T_{max}$. Table 4 displays this data, and we will continue to refer to it throughout this section.

As seen in the plasma curves, the formulations containing spray-dried drug showed much lower plasma levels than the formulations with micronized drug. Within the spray-dried group, relative bioavailability was 40% for the SD formulation and 31% for the AM formulation. T-tests performed on AUC values normalized by dose show that the absorption of SD and AM were statistically different, with p=0.03. Additionally, the $C_{max}$ of the SD formulation was almost double that of the encapsulated version, which illustrates the degree of control that the polymer can offer to reduce absorptive bursts. $T_{max}$ was also prolonged in the AM formulation, again probably because of the modulation of the polymer coating.

TABLE 4

Pharmacokinetic Analysis

| Formulation | Drug Dose (mg/kg) | AUC (µg-hour/ml) | Relative Bioavailability | $C_{max}$ (µg/mL) | $T_{max}$ (hours) |
|---|---|---|---|---|---|
| IV | 24 | 2116 ± 155 | 100 ± 0.0% | 178 ± 16.5 | 1.0 ± 0.0 |
| SD | 25 | 1283 ± 102 | 58 ± 7.5% | 91 ± 5.0 | 2.8 ± 0.8 |
| AM | 25 | 916 ± 85 | 41.0 ± 7.0% | 48.5 ± 10.4 | 5.8 ± 1.4 |
| MDAP | 5 | 576 ± 148 | 131.2 ± 33.8% | 35.0 ± 7.0 | 5.5 ± 2.5 |
| MDAP | 15 | 1175 ± 239 | 89.6 ± 18.8% | 60.0 ± 8.5 | 2.3 ± 0.3 |
| MDAP | 23 | 2247 ± 197 | 110.5 ± 6.7% | 95.8 ± 6.5 | 7.4 ± 1.1 |
| AN | 3.6 | 480 ± 87 | 110.8 ± 4.6% | 24.3 ± 4.8 | 5.3 ± 1.4 |
| AN | 10.9 | 1095 ± 140 | 149.5 ± 27.6% | 38 ± 5.7 | 7.0 ± 1.0 |
| AN | 18.2 | 1848 ± 164 | 113.8 ± 14.6% | 67 ± 3.4 | 10.4 ± 0.6 |
| NN | 30.6 | 1430 ± 128 | 25.3 ± 3.3% | 97 ± 9.5 | 3.7 ± 0.7 |

Most of the formulations containing the ultra-micronized drug were significantly higher in relative bioavailability than the spray-dried formulations. T-tests comparing the normalized AUCs of MDAP and AN to both SD and AM showed statistical significance between the two groups of formulations, with p values ranging from 0.001 to 0.05. The nonadhesive NN formulation was also considerably lower than MDAP and AN using the micronized drug, and p<0.05 from t-tests comparing NN to these other formulations.

The micronized drug with 7% FA:SA, MDAP, improved the relative bioavailability of dicumarol to 76.5%. $C_{max}$ was relatively high, at 95.8 µg/mL, and peak concentrations were seen in the plasma early in the experiment, with a $T_{max}$ of 7.4 hours. The addition of a higher content of FA:SA further improved these parameters. The drug fully encapsulated in p(FA:SA), AN, showed a reduction in $C_{max}$ to 67 µg/mL and $T_{max}$ is increased to 10.4 hours. The pronounced modulation of both $C_{max}$ and $T_{max}$ can be attributed to the bioadhesion afforded by FA:SA.

NN, containing the non-adhesive polymer coating, significantly decreased the relative bioavailability to 37%. Additionally, t-tests using normalized AUCs revealed p<0.05 between NN and all other formulations containing micronized drug. The other two virtues of the bioadhesive coating, control of $C_{max}$ and prolongation of $T_{max}$, also disappeared compared to the adhesive AN formulation, as $C_{max}$ increased from 67 µg/mL to 97 µg/mL and $T_{max}$ dropped from 10.4 hours to 3.7 hours.

The dose escalation studies showed that with both AN and MDAP, the lowest dose was absorbed most efficiently, and relative bioavailability reached 100% and 91% respectively. As the dose was increased, relative bioavailability decreased, especially in the MDAP group, where it fell to 62% at a dose of 15 mg/kg. Levels improved to a more reasonable figure of 77% at 23 mgkg. AN also showed a decrease in relative bioavailability as the dose was increased, but it leveled off at around 79% in this case. $C_{max}$ rose with each increasing dose in both cases, and $T_{max}$, rose proportionally only in the AN formulation.

Bioactivity: All of the formulations presented tested positive for drug activity, with PTT times of samples taken at the time point corresponding to the $T_{max}$ all exceeding 90 seconds compared to the normal range of 12 to 17 seconds.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for micronizing a hydrophobic agent, comprising:
    dissolving a hydrophobic agent in an effective amount of a first solvent, with a polymer, wherein the hydrophobic agent and the first solvent form a mixture having a continuous phase, introducing a second solvent into the mixture, and introducing an aqueous solution into the mixture wherein the aqueous solution causes precipitation of the hydrophobic agent to produce a composition of micronized hydrophobic agent having an average particle size of 1 micron or less.

2. The method of claim 1, wherein the preparation contains less than 5% polymer.

3. The method of claim 1, wherein the polymer is removed by the aqueous solution.

4. The method of claim 1, further comprising preparing microparticles by spray drying the micronized hydrophobic agent.

5. The method of claim 1, further comprising preparing microparticles of the micronized hydrophobic agent by a method selected from the group consisting of: interfacial condensation, hot melt encapsulation, and phase separation encapsulation.

6. The method of claim 1, further comprising preparing microparticles by performing phase inversion nanoencapsulation on the micronized hydrophobic agent.

7. The method of claim 1, wherein the second solvent is an alcohol.

8. The method of claim 7, wherein the alcohol is selected from the group consisting of: methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1- ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, and 3,5-pentanediol.

9. The method of claim 7, wherein the alcohol is isopropanol.

10. The method of claim 1, wherein the second solvent is a mixture of alcohols.

11. The method of claim 10, wherein the mixture of alcohols comprises: two or more of the alcohols selected from the group consisting of: methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, and 3,5-pentanediol.

12. The method of claim 1, wherein greater than 90% of the micronized hydrophobic agent have a particle size less than 1 micron.

13. The method of claim 1, wherein the hydrophobic agent is dissolved by heating the hydrophobic agent in the first solvent.

14. The method of claim 1, wherein the hydrophobic agent is dissolved by sonicating the hydrophobic agent in the first solvent.

15. The method of claim 1, wherein the hydrophobic agent is dissolved by high shearing the hydrophobic agent in the first solvent.

16. The method of claim 1, wherein the hydrophobic agent is dissolved by high stirring the hydrophobic agent in the first solvent.

17. A preparation of micronized hydrophobic agent prepared according to the method of claim 1.

18. A composition, comprising a preparation of micronized hydrophobic agent having an average particle size of less than 1 micron, wherein the preparation is composed of less than 5% polymer carrier and is free of surfactant.

19. A composition, comprising a preparation of micronized hydrophobic agent having an average particle size of less than 1 micron, wherein the preparation is free of polymer carrier and wherein the crystallinity of the micronized hydrophobic agent is at least 50% of the crystallinity of the non-micronized hydrophobic agent.

20. A method for delivering an agent to a subject, comprising:
orally administering a solid preparation of micronized hydrophobic agent having an average particle size of less than 1 micron, wherein the preparation is composed of less than 5% polymer and is free of surfactant.

21. A method for delivering an agent to a subject, comprising:
administering microparticles of a micronized hydrophobic agent encapsulated by phase inversion nanoencapsulation having an average particle size of less than 1 micron, wherein the preparation is composed of less than 5% polymer and is free of surfactant.

22. A method for achieving 100% bioactivity comprising:
orally administering to the subject a solid preparation of micronized hydrophobic agent having an average particle size of less than 1 micron and wherein 100% of the orally administered agent is bioactive.

* * * * *